(12) United States Patent
Choi et al.

(10) Patent No.: US 11,478,555 B2
(45) Date of Patent: Oct. 25, 2022

(54) CHIMERIC ANTIGEN RECEPTOR TO WHICH ANTI-COTININE ANTIBODY IS LINKED, AND USE THEREOF

(71) Applicant: SEOUL NATIONAL UNIVERSITY R&DB FOUNDATION, Seoul (KR)

(72) Inventors: Kyungho Choi, Goyang-si (KR); Hyung-Bae Park, Seoul (KR); Ji Eun Lee, Goyang-si (KR); Yumi Oh, Goyang-si (KR); Ki-Hyun Kim, Seoul (KR); Soohyun Kim, Seoul (KR); Hyori Kim, Seoul (KR); Junho Chung, Seongnam-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 162 days.

(21) Appl. No.: 15/753,212

(22) PCT Filed: Aug. 17, 2016

(86) PCT No.: PCT/KR2016/009047
§ 371 (c)(1),
(2) Date: Feb. 16, 2018

(87) PCT Pub. No.: WO2017/030370
PCT Pub. Date: Feb. 23, 2017

(65) Prior Publication Data
US 2018/0256744 A1 Sep. 13, 2018

Related U.S. Application Data

(60) Provisional application No. 62/205,844, filed on Aug. 17, 2015.

(51) Int. Cl.
| | | |
|---|---|---|
| A61K 35/17 | (2015.01) | |
| A61K 47/68 | (2017.01) | |
| C12N 15/85 | (2006.01) | |
| A61K 39/395 | (2006.01) | |
| A61K 38/17 | (2006.01) | |
| C07K 16/16 | (2006.01) | |
| C07K 16/28 | (2006.01) | |
| A61P 35/00 | (2006.01) | |

(52) U.S. Cl.
CPC .......... *A61K 47/6819* (2017.08); *A61K 35/17* (2013.01); *A61K 38/17* (2013.01); *A61K 39/395* (2013.01); *A61K 39/39558* (2013.01); *C07K 16/16* (2013.01); *C07K 16/2809* (2013.01); *C07K 16/2818* (2013.01); *C12N 15/85* (2013.01); *A61P 35/00* (2018.01); *C07K 2317/53* (2013.01); *C07K 2317/622* (2013.01); *C07K 2317/73* (2013.01); *C07K 2319/02* (2013.01); *C07K 2319/03* (2013.01); *C07K 2319/10* (2013.01)

(58) Field of Classification Search
CPC ...................................................... A61K 35/17
See application file for complete search history.

(56) References Cited

U.S. PATENT DOCUMENTS

| | | | | |
|---|---|---|---|---|
| 2004/0043401 | A1* | 3/2004 | Sadelain | C07H 21/04 435/6.16 |
| 2008/0226650 | A1* | 9/2008 | Park | C07K 16/44 530/387.9 |
| 2013/0287752 | A1 | 10/2013 | Davila et al. | |
| 2014/0056926 | A1 | 2/2014 | Chung et al. | |
| 2015/0051266 | A1 | 2/2015 | Kochenderfer et al. | |
| 2015/0238631 | A1 | 8/2015 | Kim et al. | |
| 2016/0075784 | A1 | 3/2016 | Yu et al. | |
| 2016/0130357 | A1* | 5/2016 | Mukherjee | A61K 39/39558 435/455 |
| 2018/0066034 | A1* | 3/2018 | Ma | A61K 39/39 |
| 2019/0365815 | A1 | 12/2019 | Choi et al. | |

FOREIGN PATENT DOCUMENTS

| | | | |
|---|---|---|---|
| CN | 103483453 A | * | 1/2014 |
| EP | 2 700 653 A2 | | 2/2014 |
| JP | 2011-509084 A | | 3/2011 |

(Continued)

OTHER PUBLICATIONS

Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Winkler et al. (J. Immunol. Oct. 15, 2000; 165 (8): 4505-4514).*
Chien et al. (Proc. Natl. Acad. Sci. USA. Jul. 1989; 86 (14): 5532-5536).*

(Continued)

*Primary Examiner* — Stephen L Rawlings
(74) *Attorney, Agent, or Firm* — Sughrue Mion, PLLC

(57) ABSTRACT

The present invention relates to chimeric antibody receptors with anti-cotinine antibodies linked, and use thereof. A T cell presenting the chimeric antibody receptor on the surface secretes interferon gamma specifically for a target molecule of a cotinine-conjugated binding molecule that is added together therewith and induces cell death of the cell expressing the target molecule by the T cell. On the contrary, by administering a cytotoxic agent conjugated with cotinine, cell death of the chimeric antigen receptor T cell is induced. Therefore, if necessary, a cytotoxic agent conjugated with cotinine can be administered to remove the chimeric antigen receptor T cells that have been already administered, thereby suppressing immune side effects due to hyperactivity of T cells. Thus, the chimeric antigen receptor to which the anti-cotinine antibody is linked can be effectively and safely used for the treatment of cancer.

10 Claims, 7 Drawing Sheets

Specification includes a Sequence Listing.

(56) References Cited

FOREIGN PATENT DOCUMENTS

| | | | |
|---|---|---|---|
| KR | 10-2014-0027219 A | 3/2014 |
| WO | 2009/088805 A2 | 7/2009 |
| WO | 2012/141554 A2 | 10/2012 |
| WO | 2013/044225 A1 | 3/2013 |
| WO | 2014/100615 A1 | 6/2014 |
| WO | 2015/080981 A1 | 6/2015 |
| WO | 2016/030414 A1 | 3/2016 |
| WO | 2016/123333 A1 | 8/2016 |
| WO | 2016/126608 A1 | 8/2016 |
| WO | 2016/168773 A2 | 10/2016 |
| WO | 2017/030370 A1 | 2/2017 |

OTHER PUBLICATIONS

Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Burgess et al. (J. Cell. Biol. Nov. 1990; 111 (5 Pt. 1): 2129-38).*
Bridgeman et al. (J. Immunol. Jun. 15, 2010; 184 (12): 6938-49).*
Hudecek et al. (Clin. Cancer Res. Jun. 15, 2013; 19 (12): 3153-64).*
Urbanska et al. (Cancer Res. Apr. 1, 2012; 72 (7): 1844-52).*
Park et al. (Exp. Mol. Med. Sep. 30, 2012; 44 (9): 554-61).*
Kim et al. (BMB Rep. 2014; 47 (3): 130-4).*
Park et al. (Clin. Chim. Acta. Sep. 6, 2010; 411 (17-18): 1238-42).*
Arndt et al. (Blood. 2011; 118: 1528; pp. 1-7).*
Arndt et al. (Leukemia. Jan. 2014; 28 (1): 59-69).*
Tamada et al. (Clin. Cancer Res. Dec. 1, 2012; 18 (23): 6436-45).*
Kim et al. (J. Am. Chem. Soc. Mar. 4, 2015; 137 (8): 2832-5).*
Ma et al. (Proc. Natl. Acad. Sci. USA. Jan. 26, 2016; 113 (4): E450-8).*
Rodgers et al. teaches (Proc. Natl. Acad. Sci. USA. Jan. 26, 2016; 113 (4): E459-68).*
Eshhar et al. (Proc. Natl. Acad. Sci. USA. Jan. 15, 1993; 90 (2):720-4).*
Sadelain et al. (Cancer Discov. Apr. 2013; 3 (4): 388-98).*
Gross et al. (Proc. Natl. Acad. Sci. USA. Dec. 1989; 86 (24): 10024-8).*
Kenderian et al. (Cancer Res. Nov. 15, 2014; 74 (22): 6383-9).*
Zhao et al. (J. Immunol. 2009; 183: 5563-74).*
Albanza et al. (Mol. Ther. Nov. 1, 2017; 25 (11): 2452-65).*
Fujiwara et al. (Cells. May 9, 2020; 9 (5): 1182; pp. 1-17).*
Magistrelli et al. (Biochem. Biophys. Res. Commun. May 27, 1999; 259 (1): 34-7).*
Su et al.(Protein Expr. Purif. Jun. 2006; 47 (2): 477-82).*
Hyori Kim et al., "In vitro and in vivo application of anti-cotinine antibody and cotinine-conjugated compounds", BMB Reports, 2014, pp. 130-134, vol. 47, No. 3.
International Search Report for PCT/KR2016/009047 dated Nov. 11, 2016.
European Patent Office; Communication dated Jan. 3, 2019 in counterpart application No. 16837312.4.
Urbanska, et al., "A Universal Strategy for Adoptive Immunotherapy of Cancer through Use of a Novel T-cell Antigen Receptor", Cancer Research, Feb. 7, 2012, pp. 1844-1852, vol. 72, No. 7 (10 pages total).
Cartellieri, et al., "Switching CAR T cells on and off: a novel modular platform for retargeting of T cells to AML blasts", Blood Cancer Journal, 2016, pp. 1-8, vol. 6, No. 8 (8 pages total).
Hervé Bouchard et al., "Antibody-drug conjugates—A new wave of cancer drugs", Bioorganic & Medicinal Chemistry Letters, Oct. 13, 2014, vol. 24, No. 23, pp. 5357-5363 (6 pages total).
Duong et al., "Engineering T Cell Function Using Chimeric Antigen Receptors Identified Using a DNA Library Approach", PLos One, vol. 8, No. 5, pp. 1-10, 2013 (10 pages total).
Park et al., "Anti-cotinine CAR-modified T cells provides a novel switchable CAR platform using cotinine-conjugated adaptor molecules", The Journal of Immunology, May 1, 2017, vol. 198 (1 Supplement) 73.22, 1 page (abstract only).
International Search Report for PCT/KR2018/000310 dated Apr. 24, 2018 [PCT/ISA/210].
Heo et al., "An aptamer-antibody complex (oligobody) as a novel delivery platform for targeted cancer therapies", Journal of Controlled Release, 2016, vol. 229, pp. 1-9.
Written Opinion for PCT/KR2018/000310 dated Apr. 24, 2018 [PCT/ISA/210].
Chang et al., "A Chimeric Receptor with NKG2D Specificity Enhances Natural Killer Cell Activation and Killing of Tumor Cells", Cancer Research, vol. 73, No. 6, pp. 1777-1786, 2013 (11 pages total).

* cited by examiner

【Figure 1】
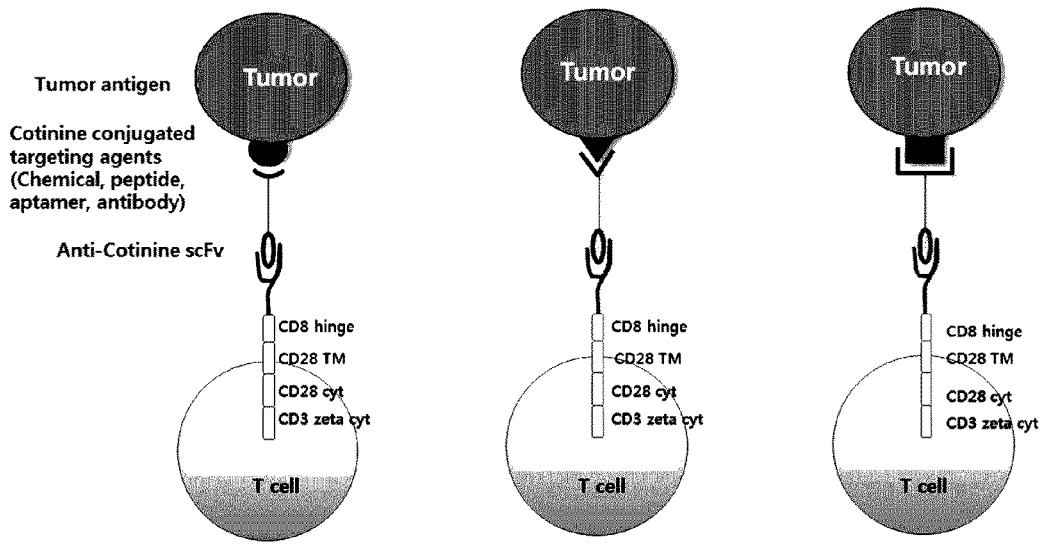
【Figure 2】
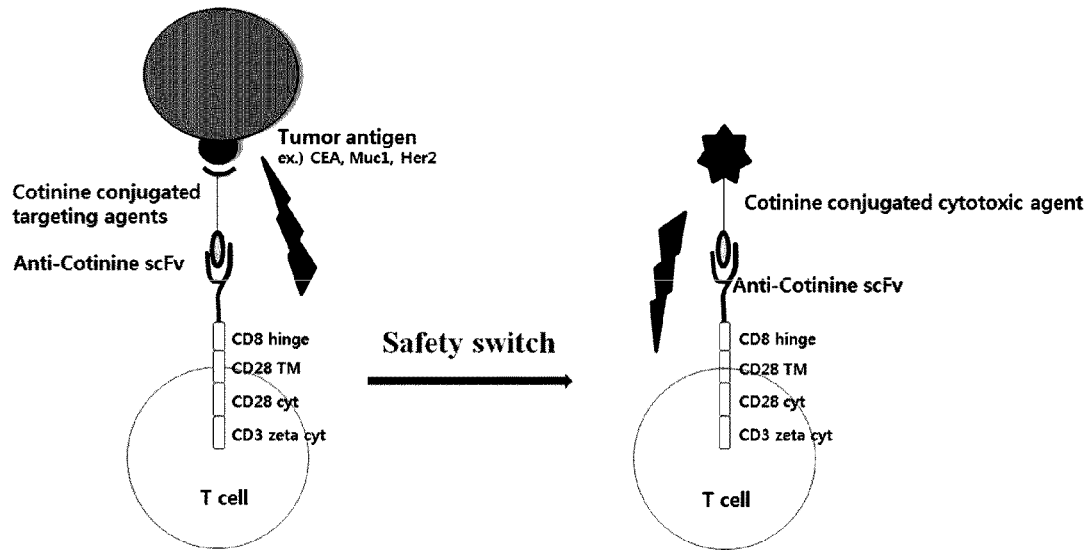

[Figure 3A]
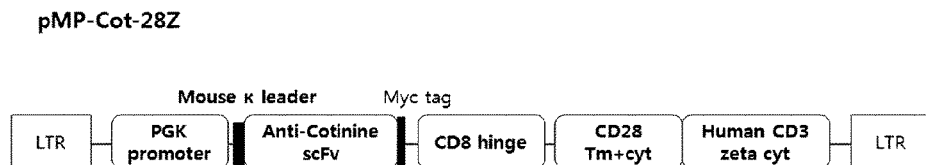
[Figure 3B]
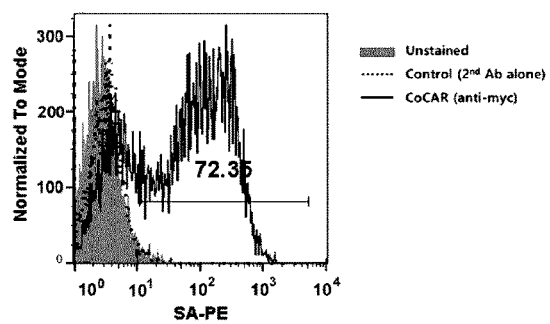
【Figure 4】
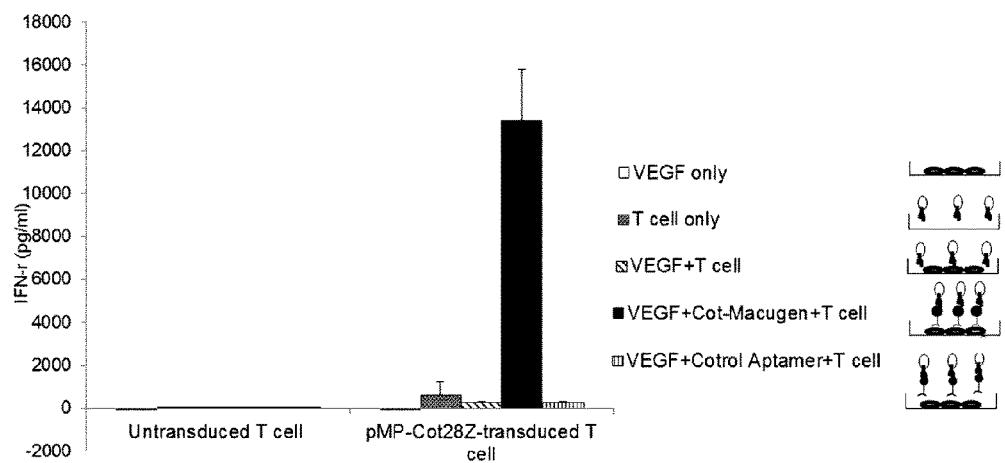

【Figure 5】
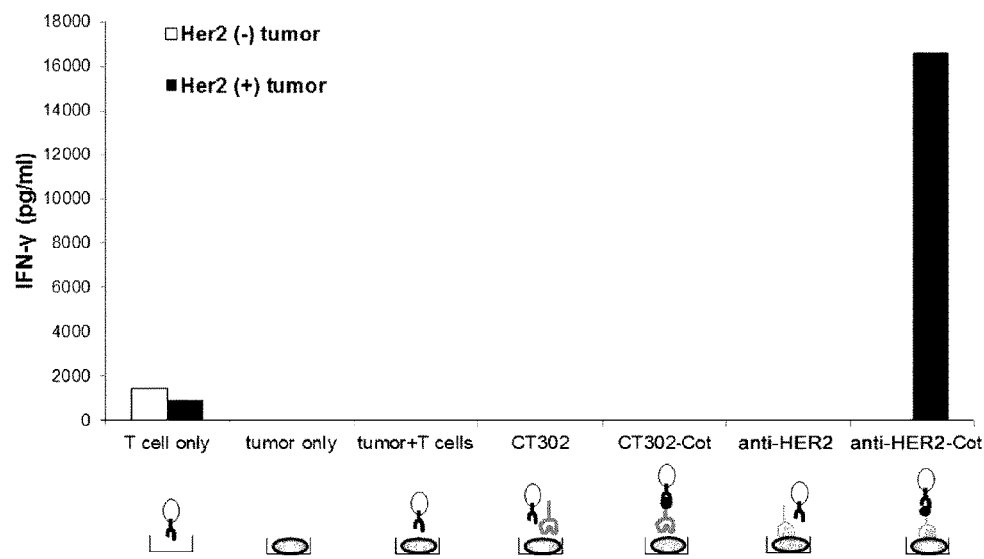
[Figure 6A]
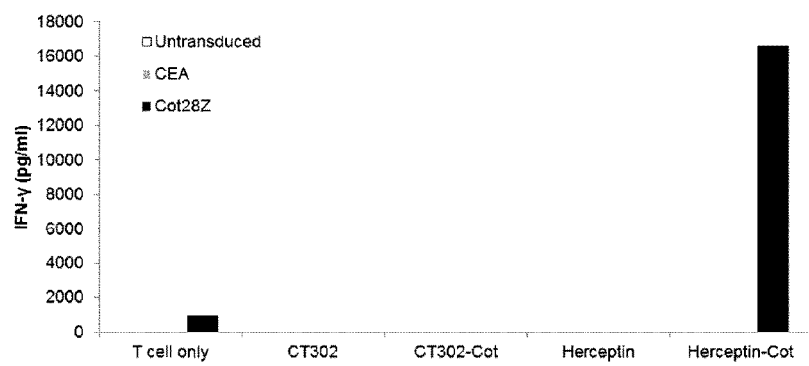
[Figure 6B]
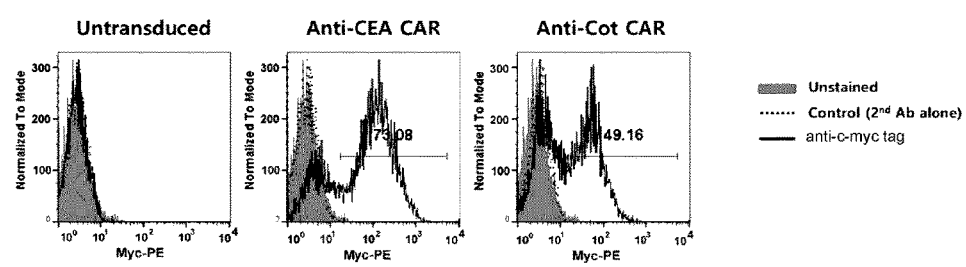

【Figure 7】
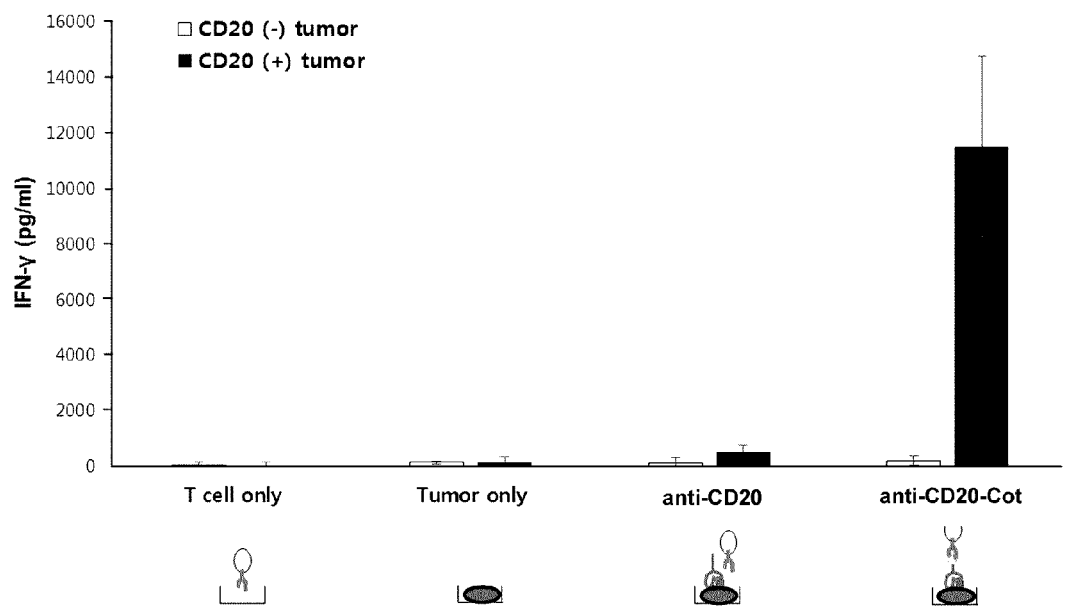
【Figure 8】
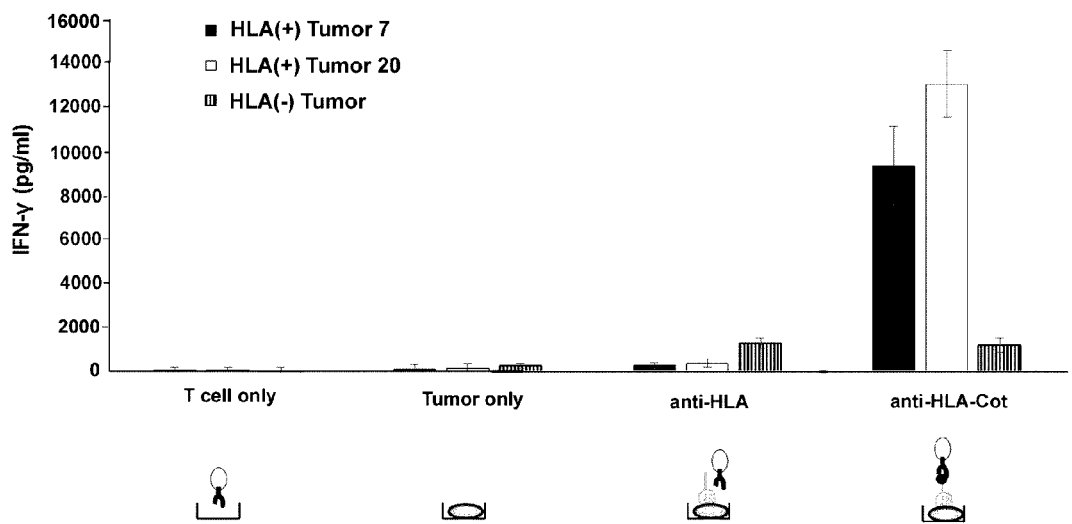

[Figure 9A]
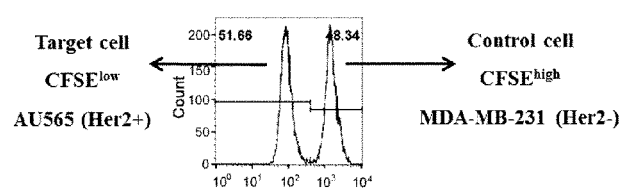
[Figure 9B]
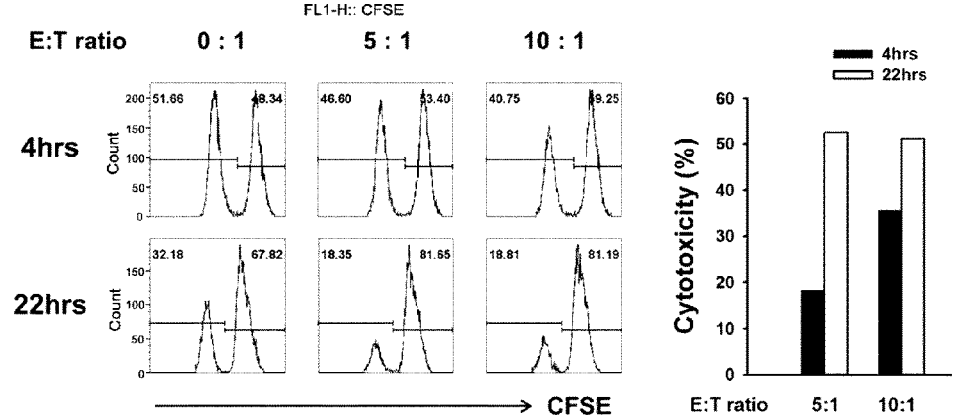

[Figure 10A]
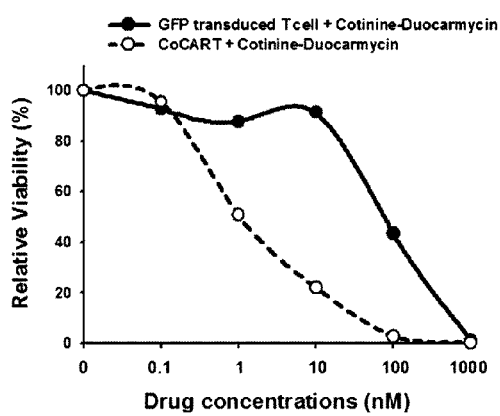
[Figure 10B]
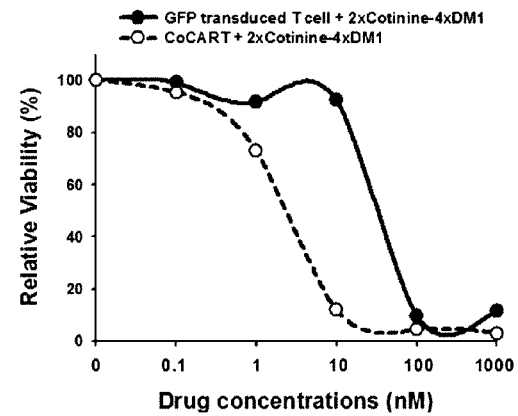
[Figure 10C]
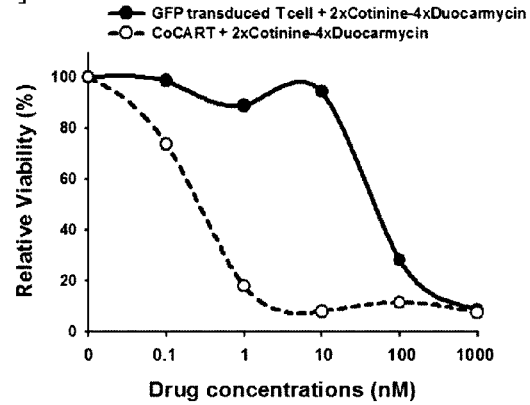

[Figure 11A] Cotinine-duocarmycin
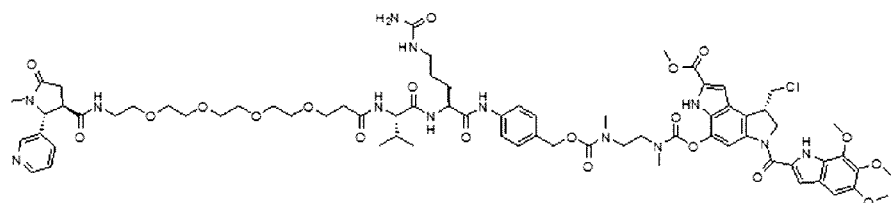
[Figure 11B] 2xCotinine-4xDM1
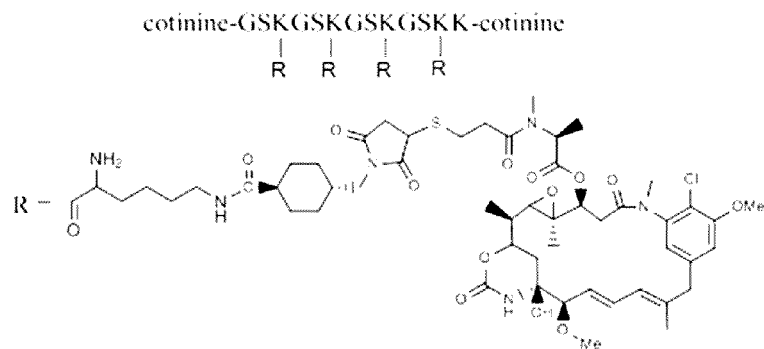
[Figure 11C] 2xCotinine-4xduocarmycin
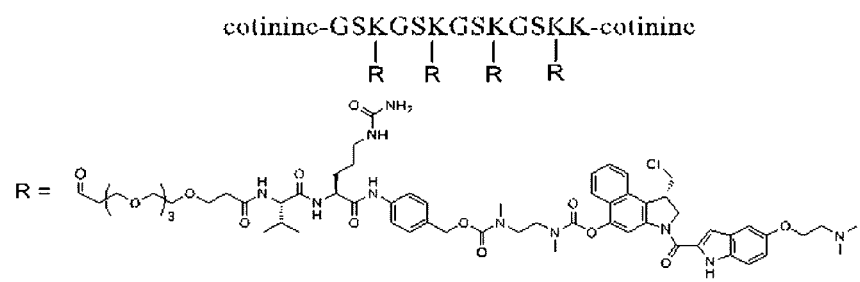

CHIMERIC ANTIGEN RECEPTOR TO WHICH ANTI-COTININE ANTIBODY IS LINKED, AND USE THEREOF

CROSS REFERENCE TO RELATED APPLICATIONS

This application is a National Stage of International Application No. PCT/KR2016/009047 filed Aug. 17, 2016, claiming priority based on U.S. Provisional Patent Application No. 62/205,844 filed Aug. 17, 2015.

TECHNICAL FIELD

The present invention relates to a chimeric antibody antigen receptor linked with an anti-cotinine antibody and a use thereof.

BACKGROUND ART

While substances such as peptides, aptamers, antibodies, etc. that can be developed as biological therapeutics have excellent effects, such substances can be easily broken down in the body and rapidly released through the kidneys, and thus have short in vivo half-lives. In order to resolve such problem, studies have been conducted to increase the in vivo half-lives of the substances by conjugating polyethylene glycol (PEG) thereto (Veronese F. M. & Pasut G., *Drug Discov. Today*, 10, 1451-1458, 2005). However, in the process of conjugating PEG, various molecular complexes are formed, and there is a limitation that optimization conditions must be established depending on binding molecules which are conjugated to PEG. In addition, such molecules have the disadvantage of having no or weak cytotoxicity when the target object thereof is a cell (e.g., a cancer cell, etc.). Therefore, recently, conjugates of an antibody and a cytotoxic agent (antibody-drug conjugates) are being developed.

Meanwhile, a chimeric antigen receptor (CAR) is composed of a portion of an antibody, a hinge region, a transmembrane domain, and an intercellular signal transduction domain. Immune cells such as T cells and natural killer cells expressing the CAR (CAR cells) specifically recognize a surface molecule that expresses on the target cells (e.g., cancer cells, etc.) using an antibody portion of the CAR, and show cytotoxicity to the target cells. Therefore, the CAR cells are utilized as a form of genetically engineered cell therapy, and in particular, it was reported that T cells expressing CAR (CAR T cells) showed a high therapeutic effect for hematological malignancies in which CD19 are expressed.

However, since conventional CAR cells have a limitation of recognizing only a single target molecule, CAR cells against haptens have been studied. These cells express CARs that recognize a specific hapten using an antibody portion of the CAR. Then, the molecules, such as peptides, aptamers, antibodies, low molecular weight chemicals, etc., that possess the binding capacity to a target molecule, are conjugated with the hapten and complexed with these anti-hapten CAR cells. Thereby, multi-targeting CAR cells can be prepared, in which one type of CAR cells can bind to various target molecules.

In order to prevent cells expressing chimeric antigen receptor from binding with non-target cells, it is preferable that the hapten be a substance which does not originally exist in vivo. In addition, the hapten must have a chemical functional group for effective conjugation with a binding molecule.

DISCLOSURE OF INVENTION

Technical Problem

Cotinine, a major metabolite of nicotine, is not biosynthesized in vivo (de novo biosynthesis) and does not show physiological activity. In addition, a metabolic process of cotinine in mammals has been well known, and it has also been reported that the serum half-life of cotinine is as short as 16 hours (Benowits N. L. et al., *3rd Handb. Exp. Pharmacol.*, 29-60, 2009). Therefore, even in the case of smokers, cotinine can be used as a hapten because cotinine is no longer present in the body after smoking has been stopped for several days. In addition, since cotinine with carboxyl functional group is easily available, cotinine conjugation to a binding molecule can be facilitated.

As such, by preparing T cells expressing CAR harboring a portion of an anti-cotinine antibody and a cotinine-conjugated binding molecule, the present inventors confirmed that the CAR T cells recognize the target of the cotinine-conjugated binding molecule specifically, secrete interferon gamma, and induce cell death of target cells (FIG. 1).

In addition, recently, along with the increased efficacy of anti-tumor CAR T cell therapy, immunotoxicity due to the overactivity of such genetically engineered T cells is being highlighted as an adverse side effect. Therefore, measures are being investigated for resolving serious adverse side effects caused by these T cells by inducing cell death of such cells when the adverse side effects develop. In the case of the anti-hapten CARs, when an immunotoxic side effect occurs in the body of a patient injected with the CAR T cells, injecting a hapten-conjugated cytotoxic agent instead of a hapten-conjugated binding molecule can induce cell death of the CAR T cells because the hapten-conjugated cytotoxic agent binds only to the anti-hapten CAR T cells. Thus, this system provides an additional advantage that the hapten-conjugated cytotoxic agent can be used as a safety measure to resolve adverse side effects caused by the T cells (FIG. 2). Accordingly, the present inventors accomplished the present invention by confirming that cell death of the chimeric antigen receptor T cells is induced by a cotinine-conjugated cytotoxic agent.

Therefore, it is an object of the present invention to provide a CAR linked with an anti-cotinine antibody.

It is another object of the present invention to provide a nucleic acid molecule encoding the CAR, an expression vector and a virus including the same, and a cell transduced with the virus.

It is still another object of the present invention to provide a CAR cell further comprising a cotinine-conjugated binding molecule in the cell.

It is still another object of the present invention to provide a pharmaceutical composition for preventing or treating a condition or a disease in which specific cells are proliferated, the pharmaceutical composition comprising the CAR cell as an active ingredient.

It is still another object of the present invention to provide a method for preventing or treating a condition or a disease in which specific cells are proliferated, the method comprising administering the CAR cell to a subject.

It is still another object of the present invention to provide a method for inducing cell death of the CAR cell.

Solution to Problem

In order to achieve the above objects, the present invention provides a CAR linked with an anti-cotinine antibody, the CAR comprising an anti-cotinine antibody or a fragment thereof, a hinge domain, a transmembrane domain, and a signal transduction domain.

In addition, the present invention provides a nucleic acid molecule encoding the CAR.

In addition, the present invention provides an expression vector comprising the nucleic acid molecule.

In addition, the present invention provides a virus comprising the nucleic acid molecule.

In addition, the present invention provides a cell transduced with the virus.

In addition, the present invention provides a CAR cell comprising a cotinine-conjugated binding molecule in the cell.

In addition, the present invention provides a pharmaceutical composition for preventing or treating a condition or a disease in which specific cells are proliferated, the pharmaceutical composition comprising the CAR cell as an active ingredient.

In addition, the present invention provides a method for preventing or treating a condition or a disease in which specific cells are proliferated, the method comprising administering the CAR cell to a subject.

In addition, the present invention provides a method for preparing a CAR cell in a subject, the method comprising administering the cell to the subject; and administering a cotinine-conjugated binding molecule to the subject.

In addition, the present invention provides a method for inducing cell death of a CAR cell, the method comprising administering the cell and a cotinine-conjugated binding molecule to a subject; and further administering a cotinine-conjugated cytotoxic agent to the subject.

Furthermore, the present invention provides a pharmaceutical kit for preventing or treating a condition or a disease in which specific cells are proliferated, the pharmaceutical kit comprising a first component containing the CAR cell as an active ingredient in a pharmaceutically and therapeutically effective amount; and a second component containing a complex of cotinine and a cytotoxic agent an as an active ingredient in a pharmaceutically and therapeutically effective amount.

Advantageous Effects of Invention

T cells, which present, on the surface thereof, the CAR linked with an anti-cotinine antibody according to the present invention, recognize the target of the cotinine-conjugated binding molecule specifically, secrete interferon gamma, and induce cell death of cells expressing the target molecule. In addition, by administering a cotinine-conjugated cytotoxic agent, cell death of the CAR T cells is induced. Accordingly, when it is necessary, it is possible to remove pre-administered CAR T cells by administering a cotinine-conjugated cytotoxic agent, thereby suppress adverse immune side effects due to overactivity of T cells. Therefore, the chimeric antigen receptor linked with an anti-cotinine antibody can be effectively used to treat a condition or a disease in which specific cells are proliferated.

BRIEF DESCRIPTION OF DRAWINGS

FIG. 1 is a diagram showing that the target of a chimeric antigen receptor T cell can be switched by changing a cotinine-conjugated binding molecule depending on a target cell.

FIG. 2 is a diagram showing that a cotinine-conjugated cytotoxic agent is used to induce cell death of chimeric antigen receptor T cells.

FIGS. 3A and 3B show the structure of a chimeric antigen receptor gene linked with an anti-cotinine antibody fragment (Cot-28Z) and a virus vector expressing the same prepared according to an embodiment of the present invention (pMP-Cot-28Z), and a graph of the results of analyzing T cells which present the chimeric antigen receptor on the surface thereof by a flow cytometer, respectively.

FIG. 4 is a graph showing the amounts of interferon gamma secreted by T cells, when chimeric antigen receptor T cells linked with the anti-cotinine antibody fragment mixed with a cotinine-conjugated anti-VEGF aptamer (Cot-Macugen) prepared according to an embodiment of the present invention are reacted to a target molecule, VEGF protein.

FIG. 5 is a graph showing the amounts of interferon gamma secreted by T cells, when the chimeric antigen receptor T cells mixed with a cotinine-conjugated anti-HER2 antibody (anti-HER2-Cot) prepared according to an embodiment of the present invention are added to HER2 positive or negative tumor cells.

FIGS. 6A and 6B are a graph confirming the HER2-positive tumor-specific interferon gamma production of the chimeric antigen receptor T cells mixed with a cotinine-conjugated anti-HER2 antibody (Herceptin-cot) prepared according to an embodiment of the present invention, and a graph showing the results of analyzing chimeric antigen receptors expressed on the surface of T cells by a flow cytometer respectively.

FIG. 7 is a graph showing the amounts of interferon gamma secreted by T cells, when the chimeric antigen receptor T cells mixed with a cotinine-conjugated anti-CD20 antibody (anti-CD20-cot) prepared according to an embodiment of the present invention are added to CD20 positive or negative tumor cells.

FIG. 8 is a graph showing the amounts of interferon gamma secreted by T cells, when the chimeric antigen receptor T cells mixed with a cotinine-conjugated anti-HLA antibody (anti-HLA-cot) prepared according to an embodiment of the present invention are added to HLA positive or negative tumor cells.

FIG. 9A is a graph showing target cells stained to show fluorescence having different intensities and FIG. 9B is a graph showing the results of adding the chimeric antigen receptor T cells prepared and a cotinine-conjugated anti-HER2 antibody according to an embodiment of the present invention to the target cells, and analyzing the target cell-specific cell death effect of the chimeric antigen receptor T cells by a flow cytometer.

FIGS. 10A-10C are graphs showing the cell death-inducing effect of the chimeric antigen receptor T cells by a cotinine-conjugated cytotoxic agent (A: cotinine-duocarmycin single conjugate, B: cotinine-DM1 complex conjugate (2×cotinine-4×DM1), and C: cotinine-duocarmycin complex conjugate (2×cotinine-4×duocarmycin)).

FIGS. 11A-11C are a set of diagrams showing the structures of cytotoxic agents used in an embodiment of the present invention (A) a cotinine-duocarmycin single conjugate, (B) a cotinine-DM1 complex conjugate, and (C) a cotinine-duocarmycin complex conjugate.

BEST MODE FOR CARRYING OUT THE INVENTION

Hereinafter, the present invention will be described in detail.

The present invention provides a chimeric antigen receptor linked with an anti-cotinine antibody, the chimeric antigen receptor comprising an anti-cotinine antibody or a fragment thereof, a hinge domain, a transmembrane domain, and a signal transduction domain.

The chimeric antigen receptor linked with the anti-cotinine antibody may be in a form in which an anti-cotinine antibody or a fragment thereof, a hinge domain, a transmembrane domain, and a signal transduction domain are linked in this order in the direction from the N-terminus to the C-terminus.

The anti-cotinine antibody is an antibody that binds to cotinine, and the antibody may be any one of a monoclonal antibody, a polyclonal antibody, or a recombinant antibody. In addition, the antibody may be an antibody in a full-length form or a fragment thereof. Here, the fragment of an antibody may comprise a part of an anti-cotinine antibody capable of binding to cotinine. The fragment of an antibody may be Fab, Fab', F(ab')2, Fv, or scFv.

The anti-cotinine antibody or a fragment thereof may include a heavy chain variable region which includes CDR1, CDR2, or CDR3, where CDR1, CDR2, and CDR3 are complementarity determining regions (CDR) represented by the amino acid sequences of SEQ ID NOs: 23 to 25, respectively, or a light chain variable region including CDR1, CDR2 or CDR3, where CDR1, CDR2, and CDR3 are represented by the amino acid sequences of SEQ ID NOs: 26 to 28, respectively. Specifically, the above-mentioned anti-cotinine antibody or a fragment thereof may include a heavy chain variable region including CDR1, CDR2, and CDR3 represented by the amino acid sequences of SEQ ID NOs: 23 to 25, respectively, and a light chain variable region including CDR1, CDR2, and CDR3 represented by the amino acid sequences of SEQ ID NOs: 26 to 28, respectively. In an embodiment of the present invention, the anti-cotinine antibody may be a scFv fragment having an amino acid sequence of SEQ ID NO: 1. In addition, the anti-cotinine antibody may be at least 80%, 85%, 90%, 95%, 97%, 98%, or 99% identical to the amino acid sequence of SEQ ID NO: 1.

The anti-cotinine antibody or a fragment thereof according to the present invention can be prepared by modifying the method described in U.S. Pat. No. 8,008,448.

The hinge domain is a domain for connecting an anti-cotinine antibody or a fragment thereof and a transmembrane domain, and may include a cysteine residue. The cysteine residue may be involved in the binding of a hinge domain to an antibody. For example, the hinge domain may be a CD8 hinge domain, an IgG1 hinge domain, an IgG4 hinge domain, a CD28 extracellular domain, a killer immunoglobulin-like receptor (KIR) extracellular domain, or a combination thereof (*Mol. Ther*, 2015(23):757; *J. Immunother*, 2006(29):284; *Cancer Immunol. Res.*, 3(7):815-26; *Blood*, 2013(122):2965). The CD8 hinge domain may have an amino acid sequence of SEQ ID NO: 3. In addition, the CD8 hinge domain may be at least 80%, 85%, 90%, 95%, 97%, 98%, or 99% identical to the amino acid sequence of SEQ ID NO: 3.

The transmembrane domain may connect the hinge domain of the chimeric antigen receptor and the signal transduction domain. The transmembrane domain may penetrate cell membranes of cells such that the anti-cotinine antibody of the chimeric antigen receptor or a fragment thereof is located on the surface of the cells and the signal transduction domain is located intracellularly. The transmembrane domain may be a transmembrane region of the CD3 zeta, CD4, CD8, CD28, or KIR protein (*Immunol. Rev.*, 2014(257):107; *J. Immunol.*, 2010(184): 6938; *Blood*, 2013 (122): 2965, *J. Immunother*, 2006(29):284; *Cancer Immunol. Res.*, 3(7):815-26). In an embodiment of the present invention, the transmembrane domain may include a transmembrane region and a cytoplasmic region of CD28, and the domain may have an amino acid sequence of SEQ ID NO: 5 or SEQ ID NO: 7. In addition, the transmembrane domain may be at least 80%, 85%, 90%, 95%, 97%, 98%, or 99% identical to the amino acid sequence of SEQ ID NO: 5 or SEQ ID NO: 7.

The signal transduction domain receives a signal provided by an anti-cotinine antibody or a fragment thereof and plays a role in transmitting the signal into the cell to which the chimeric antigen receptor is bound. The signal transduction domain may be CD3 zeta, CD278 (inducible T-cell costimulator, ICOS), CD28, CD134 (OX40), CD137 (4-1BB), killer immunoglobulin-like receptor (KIR), or DNAX activation protein 12 (DAP12) (*J. Immunol.*, 2004(172):104; *Mol. Ther*, 2013(21):2268; *Proc. Natl. Acad Sci. USA*, 2009(106): 3360; *Cancer Immunol. Res.*, 3(7):815-26). Specifically, the signal transduction domain may be a cytoplasmic region of CD28 and CD3 zeta, or a cytoplasmic region of CD137 (4-1BB) and CD3 zeta.

In an embodiment of the present invention, the signal transduction domain may be a cytoplasmic region of CD28 and CD3 zeta. The cytoplasmic region of CD28 may have an amino acid sequence of SEQ ID NO: 9 or SEQ ID NO: 11, and the cytoplasmic region of CD3 zeta may have an amino acid sequence of SEQ ID NO: 13. In addition, the signal transduction domain may be at least 80%, 85%, 90%, 95%, 97%, 98%, or 99% identical to the amino acid sequence of SEQ ID NO: 9, SEQ ID NO: 11 or SEQ ID NO: 13.

Furthermore, the chimeric antigen receptor of the present invention may include a modified form of the antibody and the domain as described above. Here, the modification may be carried out by substituting, deleting, or adding one or more amino acids of the amino acid sequence of a wild-type antibody and domain without modifying the function of the antibody and the domain. Conventionally, the substitution may be alanine or may be carried out by conservative amino acid substitution which does not affect the charge, polarity, or hydrophobicity of the whole protein. In an embodiment of the present invention, the chimeric antigen receptor may have an amino acid sequence of SEQ ID NO: 15 or SEQ ID NO: 17. In the sequence of SEQ ID NO: 15, amino acid residues at positions 22-266 correspond to scFv (SEQ ID NO: 1), amino acid residues at positions 286-348 correspond to CD8 hinge (SEQ ID NO: 3), amino acid residues at positions 349-376 correspond to human CD28 transmembrane domain (SEQ ID NO: 5), and amino acid residues at positions 377-417 and 420-531 each correspond to human CD28 cyt (SEQ ID NO: 9) and human CD3 zeta cyt (SEQ ID NO: 13), respectively. In the sequence of SEQ ID NO: 17, amino acid residues at positions 22-266 correspond to scFv (SEQ ID NO: 1), amino acid residues at positions 286-348 correspond to CD8 hinge (SEQ ID NO: 3), amino acid residues at positions 349-378 correspond to mouse CD28 transmembrane domain (SEQ ID NO: 7), and amino acid residues at positions 379-419 and 422-533 each correspond to mouse CD28 cyt (SEQ ID NO: 11) and CD3 zeta cyt (SEQ ID NO: 13), respectively. Human CD8 hinge and mouse CD8 hinge share the same sequence of SEQ ID NO: 3, and human CD3 zeta cyt and mouse CD3 zeta cyt share the same sequence of SEQ ID NO: 13. In addition, the chimeric antigen receptor may be at least 80%, 85%, 90%, 95%, 97%, 98%, or 99% identical to the amino acid sequence of SEQ ID NO: 15 or SEQ ID NO: 17.

In addition, the present invention provides a nucleic acid molecule encoding the chimeric antigen receptor.

The nucleic acid molecule according to the present invention may encode the anti-cotinine antibody or a fragment thereof (SEQ ID NO: 2), the hinge domain (SEQ ID NO: 4), the transmembrane domain (SEQ ID NO: 6 or 8), and the signal transduction domain (SEQ ID NO: 10, 12, or 14) described above. Here, the nucleic acid molecule encoding the chimeric antigen receptor according to the present invention may be a nucleotide sequence of SEQ ID NO: 16 or SEQ ID NO: 18. Here, the nucleotide sequence may include another substituted nucleotide sequence capable of expressing the antibody or domain of SEQ ID NO: 1, SEQ ID NO: 3, SEQ ID NO: 5, SEQ ID NO: 7, SEQ ID NO: 9, SEQ ID NO: 11, or SEQ ID NO: 13. In addition, the nucleic acid molecule may include a nucleic acid molecule encoding the antibody or the domain in the modified form as described above.

In addition, the present invention provides an expression vector including the nucleic acid molecule.

The expression vector may be an adenovirus vector, a retrovirus vector, a lentiviral vector, or an adeno-associated virus vector. In an embodiment of the present invention, the expression vector may be a retrovirus vector. The expression vector may be prepared by those skilled in the art such that the chimeric antigen receptor according to the present invention is expressed and secreted.

The expression vector may further include a signal sequence or a leader sequence. In an embodiment of the present invention, the leader sequence may be an immunoglobulin kappa leader sequence. The immunoglobulin kappa leader sequence may have an amino acid sequence of SEQ ID NO: 19, and may be at least 80%, 85%, 90%, 95%, 97%, 98%, or 99% identical to the amino acid sequence of SEQ ID NO: 19.

The present invention also provides a virus comprising the nucleic acid molecule.

The virus may include, in the genome thereof, a nucleic acid molecule encoding the chimeric antigen receptor according to the present invention. Therefore, a cell transduced with the virus may express the chimeric antigen receptor according to the present invention, in which an anti-cotinine antibody or a fragment thereof is located on the surface thereof. The virus may be an adenovirus, a retrovirus, a lentivirus, or an adeno-associated virus. In an embodiment of the present invention, the virus may be a retrovirus.

The virus may be obtained by transfecting cells with the expression vector as described above together with an expression vector comprising a nucleic acid molecule encoding a viral envelope protein. Here, transfection can be carried out by a conventional method. For transfection, the envelope protein that can be used may be VSV-G, an ecotropic envelope, Mokola, Rabies, MLV-Ampho, MLV-10A1, LCMV-WE, LCMV-Arm53b envelope, feline endogenous gamma retrovirus RD114 envelope and a variant thereof, gibbon ape leukemia virus (GALV) envelope and a variant thereof, MLU 4070A envelope, or gp120/gp41 (*Mol. Ther Methods Clin. Dev.*, 2016(3):16017; *J. Virol. Methods*, 2004:122-131; *Molecular Therapy-Methods & Clinical Development* 2016(3):16017).

In addition, the present invention provides a cell transduced with the virus as described above.

The cell may be transduced with a virus comprising a nucleic acid capable of expressing the chimeric antigen receptor according to the present invention. The transduced cell may have an anti-cotinine antibody or a fragment thereof located on the surface of the cell, and when cotinine binds to the antibody or the fragment thereof via antigen-antibody binding, cellular activity may be induced through intracellular signal transduction. Here, the cell may be a T cell, a natural killer cell, or a macrophage. In an embodiment of the present invention, the cell may be a T cell.

In addition, the present invention provides a chimeric antigen receptor cell further comprising a binding molecule to which cotinine is conjugated.

In the cotinine-conjugated binding molecule, when the binding molecule is an antibody, the complex may be formed via a bond between the carboxyl group of cotinine and the amine group of the antibody.

The cotinine, being a hapten, may bind to an antibody that specifically recognizes cotinine without changing the properties of the cotinine-conjugated binding molecule. Specifically, the binding molecule may be a peptide, a nucleic acid, a protein, or a chemical substance. The nucleic acid may be an aptamer, and the protein may be an antibody or a hormone. In an embodiment of the present invention, the aptamer may be an anti-VEGF aptamer. In addition, in an embodiment of the present invention, the antibody may be an anti-HER2 antibody, an anti-CD20 antibody, or an anti-HLA antibody.

The chimeric antigen receptor cell may harbor the anti-cotinine antibody or the fragment thereof linked to the cell. When the cotinine conjugates bind to an anti-cotinine antibody or a fragment thereof, they may induce cellular activities. Here, the binding of the cell and cotinine-conjugated binding molecule may be an antigen-antibody binding between the anti-cotinine antibody of the chimeric antigen receptor or a fragment thereof and cotinine. In addition, the cellular activity may be cell death-inducing activity by cytotoxic T cells.

The chimeric antigen receptor cell may be prepared through a step of adding a cotinine-conjugated binding molecule to the cell in which a chimeric antigen receptor linked with an anti-cotinine antibody or a fragment thereof expresses, and a step of selecting a chimeric antigen receptor cell complexed with the binding molecule.

In addition, the present invention provides a pharmaceutical composition for preventing or treating a condition or a disease in which specific cells are proliferated, comprising the chimeric antigen receptor cell as an active ingredient.

The chimeric antigen receptor cell used as the active ingredient of the pharmaceutical composition is as described above.

The condition or disease may be cancer, and the cancer may be solid cancer or hematologic malignancy. Here, the solid cancer may be lung cancer, colon cancer, prostate cancer, thyroid cancer, breast cancer, brain cancer, head and neck cancer, esophageal cancer, skin cancer, melanoma, retinoblastoma, thymic cancer, gastric cancer, colorectal cancer, liver cancer, ovarian cancer, uterine cancer, bladder cancer, rectal cancer, gall bladder cancer, bile duct cancer, or pancreatic cancer. In addition, the hematologic malignancy may be lymphoma, leukemia, or multiple myeloma.

The pharmaceutical composition may comprise 10 to 95 wt % of the chimeric antigen receptor cells according to the present invention as an active ingredient based on the total weight of the pharmaceutical composition. In addition to the above-mentioned active ingredient, the pharmaceutical composition of the present invention may further include one or more types of active ingredients exhibiting the same or similar functions.

In addition to the active ingredients described above, the pharmaceutical composition according to the present invention may further comprise one or more types of pharmaceutically acceptable carriers for administration.

In addition, the present invention provides a method for preventing or treating a condition or a disease in which specific cells are proliferated, the method including administering the chimeric antigen receptor cell to a subject.

The chimeric antigen receptor cell is as described above. In addition, the condition or disease may be cancer, and specific cancers are as described above.

The dosage amount of the chimeric antigen receptor cell according to the present invention may be adjusted according to various factors such as the type of a disease, the severity of a disease, the type and content of active ingredients and other ingredients included in the pharmaceutical composition, the type of dosage form and the age, body weight, general health, sex, and diet of a patient, administration time, administration route, treatment time, and concurrently used drugs. However, for desired effects, the effective amount of the chimeric antigen receptor cells included in the pharmaceutical composition according to the present invention may be $1 \times 10^5$ to $1 \times 10^{11}$ cells/kg. Here, the administration may be performed once a day and may also be divided over several times a day.

In addition, the chimeric antigen receptor cell of the present invention may be administered to a subject by various methods known in the art. The subject may be a mammal, and specifically a human. The administration route may be appropriately selected by those skilled in the art in consideration of the administration method, volume and viscosity of a body fluid, and the like.

In addition, the present invention provides a method for producing a chimeric antigen receptor cell in a subject, the method comprising administering the cell to the subject; and administering a cotinine-conjugated binding molecule to the subject.

The cell is transduced with a virus comprising a nucleic acid capable of expressing the chimeric antigen receptor according to the present invention, and is as described above. In addition, the cotinine-conjugated binding molecule is as described above.

The subject may be a mammal, and specifically a human, and administration may be appropriately carried out by those skilled in the art as described above.

In addition, the present invention provides a method for inducing cell death of a chimeric antigen receptor cell, the method comprising administering the cell and a cotinine-conjugated binding molecule to a subject; and further administering a cotinine-conjugated cytotoxic agent to the subject.

The chimeric antigen receptor cell is as described above. In the case of an anticancer treatment using chimeric antigen receptor cells, immunotoxicity due to overactivity of the cells may occur as a side effect. Therefore, in order to resolve such a side effect, cell death of chimeric antigen receptor cells can be induced by additionally administering a cotinine-conjugated cytotoxic agent in addition to a cotinine-conjugated binding molecule.

The cytotoxic agent mentioned above may be used as long as it is a substance capable of inducing cell death. Specifically, the cytotoxic agent may be duocarmycin, SN-38, calicheamicin, monomethyl auristatin E (MMAE), monomethyl auristatin F (MMAF), doxorubicin, pyrrolobenzodiazepine, DM4, or DM1. In an embodiment of the present invention, the cytotoxic agent may be duocarmycin or DM1 (ASCO meeting abstracts 2014(32):2558; *Clin. Cancer Res.*, 2011(17):3157-69; *Leuk. Lymphoma*, 2015(56):2863-69; *J. Clin. Oncol.*, 2014(32):3619-25; *Proc. Am. Soc. Clin. Oncol.*, 2015(33):2503; *J. Drug Deliv.*, 2013(2013):898146; *Sci. Transl. Med.*, 2015(7):302ra136; *Mol, Cancer Ther.*, 2014(13):1537-48; *J. Clin. Oncol.*, 2008(26):2147-54).

Administration of the cotinine-conjugated cytotoxic agent may be adjusted by various factors as described above. The effective amount of the chimeric antigen receptor cells included in the pharmaceutical composition according to the present invention may be appropriately determined by those skilled in the art. Here, the administration may be performed once a day and may also be divided over several times a day.

Furthermore, the present invention provides a pharmaceutical kit for preventing or treating a condition or a disease in which specific cells are proliferated, the pharmaceutical kit comprising a first component containing the chimeric antigen receptor cell as an active ingredient in a pharmaceutically and therapeutically effective amount; and a second component containing a cotinine-conjugated cytotoxic agent as an active ingredient in a pharmaceutically and therapeutically effective amount.

In the pharmaceutical kit of the present invention, the first component and the second component may be administered sequentially for the prevention or treatment of a condition or a disease. In the case of sequentially administering the first component and the second component, the second component may be administered when an immunotoxic side effect appears or when the chimeric antigen receptor cells are immortalized after the administration of the first component.

The condition or disease may be cancer, and specific cancers are as described above.

MODE FOR THE INVENTION

Hereinafter, the present invention is described in detail using the examples below. The examples below are merely intended exemplify the present invention, and the scope of the present invention is not limited thereto.

Example 1. Preparation of Retrovirus Comprising Nucleic Acid Encoding Chimeric Antigen Receptor Linked with Anti-Cotinine Antibody Fragment 1-1. Preparation of Construct First, a plasmid comprising nucleic acids each encoding an scFv fragment of an anti-cotinine antibody, a hinge domain, a transmembrane domain, and a signal transduction domain was prepared by the following method.

Specifically, a scFv fragment of an anti-cotinine antibody was amplified by PCR in a conventional manner from a template plasmid using a primer including a mouse Ig kappa leader sequence. The template was a plasmid generated by ligation of an anti-cotinine scFv fragment cleaved with the SfiI restriction enzyme to a pCEP4 vector (Invitrogen, US) (*Clin. Chim. Acta.*, 2010, 411-1238). Meanwhile, the skeletal part of the chimeric antigen receptor including c-myc tag (SEQ ID NO. 21), human CD8 hinge region, transmembrane region and cytoplasmic region of mouse CD28, and a cytoplasmic region of human CD3 zeta, was amplified by PCR from the template, pLxSN-scFv-anti-CEA-CD28-zeta plasmid (Dr. Philip Darcy, PeterMac Cancer Center, Australia). Specific sequences of the primers used for the PCR are shown in Table 1 below.

TABLE 1

| Name | Sequence (5''→3') | SEQ ID Number |
|---|---|---|
| Anti-cotinine scFv forward direction | gatatcaagcttgccaccatggattttcaggtgcagattttcagcttcctgctaatcagtgcctca gtcataatgtctagagagctcgatctgacccag | SEQ ID NO: 29 |
| Anti-cotinine scFv reverse direction | tgaagagatggtgaccag | SEQ ID NO: 30 |
| CAR skeleton forward direction | gcggccgcagaacaaaaa | SEQ ID NO: 31 |
| CAR skeleton forward direction | actagtgtcgacttagcgaggggcagggc | SEQ ID NO: 32 |
| CEA CAR forward direction | gatatcaagcttccatgggccaccatggattttcaggtgcag | SEQ ID NO: 33 |
| CEA CAR reverse direction | gaattcatcgatgtcgacgcggccgcttagcgaggggcagggc | SEQ ID NO: 34 |

The two obtained PCR products were ligated to prepare cDNA of the anti-cotinine chimeric antigen receptor. The prepared cDNA and the pMSCV-puro vector (K1062-1, Clontech, US) were cleaved with HindIII/SalI and HindIII/ClaI, respectively and ligated together. As a result, the cDNA encoding the scFv fragment of the anti-cotinine antibody and the skeletal domains of chimeric antigen receptor was cloned into the position downstream of the PGK promoter of a pMSCV-puro retroviral vector, where the puromycin-resistant gene had been originally located. The prepared construct was confirmed through nucleotide sequencing analysis, and named pMP-Cot-28Z (FIG. 3A).

1-2. Preparation of Retrovirus

The retroviral construct prepared in Example 1-1 was transfected into PHOENIX™ GP (ATCC, US) cell line, along with pMD2.G plasmid (#12259, Addgene, US) which contains cDNA encoding the vesicular stomatitis Indiana virus G protein (VSV-G) as a virus envelope protein. Transfection was carried out according to the manufacturer's protocol using LIPOFECTAMINE™ 2000 (Cat. #11668-019, Invitrogen, US). After 48 hours, the culture supernatant containing the VSV-G pseudotyped retrovirus was harvested and incubated with a PHOENIX™ Eco (ATCC, US) cell line for infection with the retrovirus. Three to five days after infection, Phoenix Eco cells positively stained with fluorescence-labeled anti-myc antibody were selected using a flow cytometer (BD Bioscience, US) to establish a retrovirus-producing cell line. The retrovirus culture supernatant produced from this cell line was concentrated 10-fold using a centrifugal filter device (Amicon Ultra-15, 100 kDa cut-off, Millipore, US).

Example 2. Preparation of Cytotoxic T Cells with a Chimeric Antigen Receptor Linked with Anti-Cotinine Antibody Fragment Presented on Surface Thereof Using the virus prepared in Example 1-2, cytotoxic T cells were prepared with a chimeric antigen receptor linked with anti-cotinine antibody fragment presented on the surface thereof.

First, splenocytes were isolated from B6 mice and dispensed in a cell culture container coated with 10 µg/mL of the anti-CD3 antibody (145-2C11, BD Bioscience, US) so that there were 2.5×10$^6$ cells per well. The cells were supplemented with a total of 1 mL of the RPMI-1640 medium including 2 µg/mL of the anti-CD28 antibody (37.51, BD Bioscience, US), and cultured under conditions of 5% CO$^2$ and 37° C. After 24 hours, 1 mL of the concentrated retrovirus including 2 µL of polybrene (Sigma-Aldrich, US) at 6 mg/mL was added to the cells and transduced by centrifugation for 90 minutes at 2,500 rpm using a centrifuge (Centrifuge 5810R, Eppendorf, US). Polybrene was used to increase the transduction rate of the retrovirus. Afterwards, 1 mL of the culture supernatant was removed, 1 mL of the concentrated retrovirus and 1 µL of polybrene were added thereto, and the retrovirus was transduced by centrifugation under the same conditions as above. Afterwards, 1 mL of the culture solution was removed, and 1 mL of the RPMI-1640 medium including 20 U/mL of interleukin-2 (Gibco, US) was added.

After 48 hours, the medium of the virus-transduced T cells was replaced with a medium containing 20 U/mL of interleukin-2 and cultured for 72 hours under conditions of 5% CO$^2$ and 37° C. Afterwards, the transduction rate of the chimeric antigen receptor linked with the anti-cotinine antibody fragment was determined by measuring the percentage of cell population positively stained with fluorescence-labeled anti-c-myc antibody using a flow cytometer, which was about 50 to 70% (FIG. 3B). Meanwhile, the T cells in which the green fluorescent protein was introduced as a control group showed a transduction rate of about 80%. T cells with the thus prepared chimeric antigen receptor linked with the anti-cotinine antibody fragment presented on the surface thereof were used in the following experiments within 24 hours after preparation.

Example 3. Preparation of Complex of Cotinine and Binding Molecule 3-1. Preparation of Complex of Cotinine and Antibody As a binding molecule, cotinine-conjugates were prepared using rituximab (Genentech, Biogen, US), which is an anti-CD20 antibody, trastuzumab (Genentech, US), which is an anti-HER2 antibody, CT302 (Celltrion, Korea), which is an anti-influenza virus hemagglutinin antibody, and W6/32

(eBioscience, US), which is an anti-HLA antibody. Cotinine conjugation was performed by an EDC (1-ethyl-3-[3-dimethylaminopropyl]carbodiimide) coupling method.

First, the antibodies above were dissolved in PBS to a concentration of 25 μM. Meanwhile, trans-4-cotinine carboxylic acid (Sigma-Aldrich) was dissolved in 1 mL of the MES buffer [0.1 M MES (2-[morpholino]ethanesulfonic acid) and 0.5 M sodium chloride, pH 6.0] to a concentration of 5 mM. EDC at a concentration of 50 mM and N-hydroxysulfosuccinimide (Sulfo-NHS, Thermo Scientific, US) at a concentration of 125 mM were added to the solution, and were then mixed by stirring at room temperature for 15 minutes to prepare an active solution in which cotinine-NHS ester was formed. A sodium hydroxide solution was added to adjust the pH of the above-mentioned active solution to 7 or more for optimal reaction between the cotinine-NHS ester and the amine group of the protein, and 1 mL of this active solution was mixed with the same volume of the antibody to be conjugated with cotinine at a concentration of 25 μM. The mixture was reacted by stirring at room temperature for 3 hours to obtain a cotinine-antibody conjugates produced via an EDC coupling reaction. The cotinine-antibody conjugates thus obtained was dialyzed with PBS using the SLIDE-A-LYZER™ Dialysis Cassette (Thermo Fisher Scientific, US), or was subject to replacing the buffer solution with PBS using the AMICON® Ultra Centrifugal Filter (EMD Millipore, US).

3-2. Preparation of Complex of Cotinine and Aptamer

A cotinine-pegaptanib conjugate was prepared from pegaptanib, an aptamer that recognizes the vascular endothelial growth factor (VEGF), which was generated by the solid-phase oligopeptide synthesis method.

In detail, a pegaptanib RNA aptamer (5'-pCfpGmpGmpArpArpUfpCfpAmpGmpUfpGmpAmpAmpUfpGmp-CfpUfpUfpAmpUfp AmpCfpAmpUfpCfpCfpGm-p-dT-3-3', SEQ ID NO: 35) was synthesized from the 3'-terminus to the 5'-terminus using an oligopeptide synthesizer, and an amino C6 linker was attached to the 5'-terminus. Chemical conjugation with cotinine was performed using the active ester cross-linking method for the amino C6 linker, and then purified (>95% purity) by reverse phase high pressure liquid chromatography using an Xbridge Prep C18 column (5 μm, 10×150 mm, Waters Corp., US). The mass thereof was determined using a mass spectrometer (ST Pharm, Korea) (*Clin. Chim. Acta.*, 2010(411):1238; *Exp. Mol. Med.*, 2012 (44):554).

The synthesized pegaptanib cotinine-conjugate suspended in distilled water containing diethyl pyrocarbonate was denatured at 95° C. for 5 minutes, cooled at room temperature for 30 minutes, and then stored at −20° C.

Comparative Example 1. Preparation of Chimeric Antigen Receptor T Cells Linked with Anti-Carcinoembryonic Antigen scFv Fragment A chimeric antigen receptor gene linked with the anti-carcinoembryonic antigen (anti-CEA) scFv fragment was obtained by PCR method by using the primers listed in Table 1 above using the pLxSN-scFv-anti-CEA-zeta plasmid (Dr. Philip Darcy, PeterMac Cancer Center, Australia) as a template. The obtained gene and the pMSCV-puro vector (K1062-1, Clontech, US) were cleaved with HindIII and ClaI respectively and ligated together. The prepared construct was named pMP-C28Z. Using the construct, a retrovirus was prepared under the conditions and methods of Examples 1 and 2, and T cells transduced with the retrovirus were prepared.

Comparative Example 3. Preparation of T Cells Expressing Green Fluorescent Protein In order to prepare T cells expressing the green fluorescent protein, the gene of the green fluorescent protein (GFP) included in the pMIG-w plasmid (Dr. Yosef Refaeli, National Jewish Medical and Research Center, US) was obtained by digestion of the plasmid with NcoI and SalI. The digested GFP gene fragment was inserted into the NcoI/SalI site of the pMP-C28Z plasmid prepared in Comparative Example 2 after removing the anti-carcinoembryonic chimeric antigen receptor gene that was included in this plasmid. The prepared construct was named pMP-GFP. Afterwards, the construct was used to produce a retrovirus under the conditions and methods of Examples 1 and 2, and T cells transduced with the retrovirus were produced.

Test Example 1. Confirmation of Activation of Chimeric Antigen Receptor T Cells Linked with Anti-Cotinine Antibody Fragment Using Cotinine-Pegaptanib Conjugate Using the cotinine-pegaptanib conjugate prepared in Example 3-2 above, whether the conjugate recognizes the vascular endothelial growth factor (VEGF) and thereby induces activation of chimeric antigen receptor cells was examined.

First, 5 μg/mL of VEGF protein was added to a 96-well plate, and then, the plate was placed overnight at 4° C. for coating the plate with VEGF. The coated plate was washed twice with the RPMI-1640 medium (Welgene, Korea) supplemented with 20% fetal bovine serum and 1% penicillin-streptomycin (Gibco, US), and the 100-nM cotinine-pegaptanib conjugate was added and incubated at 37° C. for 1 hour. After the reaction, the plate was washed 3 times with the RPMI-1640 medium, and then the chimeric antigen receptor T cells prepared in Example 2 were added so that there were $1 \times 10^5$ cells per well, and the cells were cultured at 37° C. under 5% $CO_2$ for 24 hours. Then, the amount of interferon gamma secreted in the medium was measured according to the manufacturer's protocol using an ELISA kit (Cat #. 555138, BD Bioscience, US), and the results are shown in FIG. 4. As control groups, a group (VEGF only) in which nothing was added to a plate coated with VEGF, a group (T cell only) in which only T cells were added to a plate not coated with VEGF, a group (VEGF+T cell) in which only T cells were added to a plate coated with VEGF, and a group (VEGF+Control Aptamer+T cell) in which a control aptamer (5'-dTTGGTGGTGGTGG-TTGTGGTGGTGGTGG-3', SEQ ID NO: 36) and T cells were added to a plate coated with VEGF, were used.

As shown in FIG. 4, it was confirmed that secretion of interferon gamma was significantly increased in the group (VEGF+Cot-pegaptanib+T cell) in which the cotinine-pegaptanib conjugate was added to the chimeric antigen receptor T cells linked with the anti-cotinine antibody fragment.

Test Example 2. Confirmation of Activation of Chimeric Antigen Receptor T Cells Linked with Anti-Cotinine Antibody Fragment Using Cotinine-Anti-HER2 Antibody Conjugate Using the cotinine-anti-HER2 antibody conjugate prepared in Example 3-1, it was determined whether the conjugate induces activation of chimeric antigen receptor cells by recognizing HER2 present on cell surfaces.

First, the AU565 cell line, which is an HER2 positive cell, and the MDA-MB-231 cell line, which is an HER2 negative cell, were dispensed in wells of 96-well round bottom plate so that there were $3\times10^4$ cells per well, and were cultured overnight under conditions of 5% $CO_2$ and 37° C. After removal of the culture supernatant, 100 µL of the cotinine-anti-HER2 antibody conjugate added to a concentration 10 µg/mL in the DMEM medium (Gibco, US) supplemented with 10% fetal bovine serum and 1% penicillin-streptomycin was added, and was cultured under the same conditions for 1 hour. Thereafter, the medium was removed, the cells were washed twice with a serum-free medium, and then the chimeric antigen receptor T cells prepared in Example 2 were added so that there were $3\times10^5$ cells per well, and cultured for 24 hours under conditions of 5% $CO^2$ and 37° C. Then, the amount of interferon gamma secreted in the medium was measured according to the manufacturer's protocol using an ELISA kit, and the results are shown in FIG. 5. As control groups, a group (T cell only) in which chimeric antigen receptor T cells were added to a plate in which tumor cells were not cultured, a group (tumor only) in which nothing was added to a plate in which tumor cells were cultured, a group (tumor+T cell) in which chimeric antigen receptor T cells were added to a plate in which tumor cells were cultured, a group (CT302) in which an influenza virus hemagglutinin-specific antibody (CT302) and chimeric antigen receptor T cells were added to a plate in which cells were cultured, a group (CT302-Cot) in which cotinine-conjugated CT302 antibody and chimeric receptor T cells were added to a plate in which tumor cells were cultured, and a group (anti-HER2) in which the free anti-HER2 antibody and chimeric antigen receptor T cells were added to a plate in which cells were cultured, were used.

As shown in FIG. 5, it was confirmed that secretion of interferon gamma was significantly increased in the group (anti-HER2-Cot) in which the cotinine-anti-HER2 antibody conjugate was added to the chimeric antigen receptor T cells linked with the anti-cotinine antibody fragment.

Test Example 3. Confirmation of Antigen-Specific Activation of Chimeric Antigen Receptor T Cells Linked with Anti-Cotinine Antibody Fragment In order to determine whether secretion of interferon gamma induced by chimeric antigen receptor T cells linked with the anti-cotinine antibody fragment complexed with the cotinine-anti-HER2 antibody conjugate is specific to the antibody linked with cotinine, the following experiment was carried out.

The experiment was carried out under the same conditions and methods as in Test Example 2, except that only AU565 cells which were HER2 positive cells were used. T cells not expressing anything on the surface, T cells prepared in Comparative Example 1, or T cells prepared in Example 2 were each added in combination with a group (T cell only) in which only T cells were added to a plate in which tumor cells were not cultured, a group (CT302) in which the CT302 antibody and T cells were added to a plate in which tumor cells were cultured, a group (CT302-Cot) in which cotinine conjugated with the CT302 antibody and T cells were added to a plate in which tumor cells were cultured, a group (anti-HER2) in which the free anti-HER2 antibody and T cells were added to a plate in which cells were cultured, and a group (anti-HER2-Cot) in which cotinine conjugated with the anti-HER2 antibody and T cells were added to a plate in which tumor cells were cultured. As a result, the amount of secreted interferon gamma was measured by the ELISA method and shown in FIG. 6A.

As shown in FIG. 6A, it was confirmed that secretion of interferon gamma was significantly increased in the group (anti-HER2-Cot) in which the cotinine-anti-HER2 antibody conjugate was added to chimeric antigen receptor T cells linked with the anti-cotinine antibody fragment. Therefore, it was found that the secretion of interferon gamma was specifically induced by the binding molecule conjugated with cotinine.

Test Example 4. Confirmation of Expression of Chimeric Antigen Receptor Presented on Surface of T Cells The expression of the chimeric antigen receptor was determined by measuring the positivity of c-myc tag staining in T cells that do not express any chimeric antigen receptor on the surface and the chimeric antigen receptor T cells linked with the anti-cotinine antibody fragment or with the anti-CEA antibody fragment, prepared in Example 2 and Comparative Example 1 respectively.

First, T cells that do not express any chimeric antigen receptor on the surface and the chimeric antigen receptor T cells prepared in Example 2 or Comparative Example 1 were dispensed so that there were $4\times10^5$ cells per well. The dispensed cells were washed twice with a PBS buffer solution supplemented with 1% bovine serum albumin (BSA) and 0.02% $NaN_3$, and the anti-c-myc antibody (BD Bioscience, US) was added after diluting at a ratio of 1:400 in the buffer solution. The mixtures were reacted for 20 minutes under refrigeration and washed 3 times with the PBS buffer solution. After adding 50 µL of a PBS supplemented with streptavidin-PE (BD Bioscience, US) at a ratio of 1:1000, anti-CD8-perCP-Cy5.5 (BD Bioscience, US) at a ratio of 1:500, and anti-CD4-APC (BD Bioscience, US) at a ratio of 1:1000, the mixtures were reacted for 25 minutes under refrigeration. After being washed three times with the PBS buffer, the cells were resuspended in a total of 300 µL of PBS. c-myc positive cells were analyzed using a flow cytometer (FACS Caliber, BD Bioscience, US), and the results are shown in FIG. 6B. A group (unstained) treated with no antibody and a group (control) treated with only streptavidin-PE, which is a secondary antibody, were used as control groups for the T cells.

As shown in FIG. 6B, it was confirmed that the chimeric antigen receptor T cells prepared in Example 2 and Comparative Example 1 expressed the anti-cotinine antibody fragment or anti-CEA antibody fragment.

Test Example 5. Confirmation of Activation of Chimeric Antigen Receptor T Cells Linked with Anti-Cotinine Antibody Fragment Using Cotinine-Anti-CD20 Antibody Conjugate Using the cotinine-anti-CD20 antibody conjugate prepared in Example 3-1, it was determined whether the conjugate induces activation of chimeric antigen receptor cells by recognizing CD20 on the cell surface. Specifically, an experiment was carried out under the same conditions and methods as in Test Example 2, except that instead of the AU565 cell line and the MDA-MB-231 cell line, a Jurkat E6.1 cell line, which is a CD20 negative cell, and a Raji cell line, which is a CD20 positive cell, were cultured in the RPMI-1640 medium supplemented with 10% fetal bovine serum and 1% penicillin-streptomycin, and the amount of secreted interferon gamma was determined in a culture solution obtained after 48 hours of culturing. As a result, the amounts of secreted interferon gamma are shown in FIG. 7. A group (T cell only) in which chimeric antigen receptor T cells were added to a plate in which cells were not cultured, a group (tumor only) in which nothing was added to a plate in which tumor cells were cultured, and a group (anti-CD20) in which the anti-CD20 antibody and chimeric antigen receptor T cells were added to a plate in which cells were cultured were used as control groups.

As shown in FIG. 7, it was confirmed that secretion of interferon gamma was significantly increased in a group (anti-CD20-Cot) in which the cotinine-anti-CD20 antibody conjugate was added to the chimeric antigen receptor T cells linked with the anti-cotinine antibody fragment.

Test Example 6. Confirmation of Activation of Chimeric Antigen Receptor T Cells Linked with Anti-Cotinine Antibody Fragment Using Cotinine-Anti-HLA Antibody Conjugate Using the cotinine-anti-HLA antibody conjugate prepared in Example 3-1, it was determined whether the conjugate induces activation of chimeric antigen receptor cells by recognizing HLA on the cell surface. Specifically, the experiment was carried out under the same conditions and methods as in Test Example 2, except that instead of the AU565 cell line and the MDA-MB-231 cell line, an NIH3T3 cell line, which is an HLA negative cell, and an HLA7 or HLA20 cell line, which is an HLA positive cell, were cultured in the IMDM medium supplemented with 20% fetal bovine serum and 1% penicillin-streptomycin, and the amount of secreted interferon gamma was determined in a culture solution obtained after 48 hours of culturing.

Meanwhile, the HLA7 and HLA20 cell lines were prepared by the following method. Specifically, a mixed solution of 10 mL of peripheral blood and the same amount of PBS was dispensed to 15 mL of Ficoll-Paque PLUS (GE Healthcare Life Science, US) and centrifuged at 400×g for 30 minutes, with the brake set to "0". After centrifugation, the plasma in the uppermost layer was removed, and 5 mL of a peripheral blood mononuclear cell layer was taken. 30 mL of the RPMI-1640 medium was added thereto, and centrifugation was performed for 10 minutes under the same conditions. The supernatant was removed, and the same amount of the RPMI-1640 medium was added to perform another wash. The precipitated cells were resuspended in 2 mL of the RPMI-1640 medium including 20% fetal bovine serum, and the number of cells was counted. $1\times10^7$ cells were dispensed into a T25 flask, and a total of 6 mL of a culture medium was added and cultured under conditions of 5% $CO_2$ and 37° C. 2 mL of Epstein-Barr virus (VR-1492, ATCC, US) was added thereto and cultured under the same conditions. After two hours of culturing, 1 μg/mL of cyclosporin A (Gibco, US) was added and cultured under the same conditions for 4 days. On the $4^{th}$ day of culturing, 2 mL of a culture medium was added, and on the $7^{th}$ day, was subcultured. When B cells transduced with Epstein-Barr virus formed colonies for 10 to 20 days by continuing the subculture, two colonies were taken to continue subculturing. The two immortalized B cell lines thus prepared were named HLA7 and HLA20, respectively.

As a result, the amounts of secreted interferon gamma are shown in FIG. 8. A group (T cell only) in which chimeric antigen receptor T cells were added to a plate in which tumor cells were not cultured, a group (tumor only) in which nothing was added to a plate in which tumor cells were cultured, and a group (anti-HLA) in which the free anti-HLA antibody and chimeric antigen receptor T cells were added to a plate in which cells were cultured were used as control groups.

As shown in FIG. 8, it was confirmed that secretion of interferon gamma was significantly increased in a group (anti-HLA-Cot) in which the cotinine-anti-HLA antibody conjugate was added to the chimeric antigen receptor T cells linked with the anti-cotinine antibody fragment.

Test Example 7. Confirmation of Target Cell-Specific Apoptotic Effect by Chimeric Antigen Receptor T Cells Linked with Cotinine-Anti-HER2 Antibody Conjugate and Anti-Cotinine Antibody Fragment Using the chimeric antigen receptor T cells linked with the anti-cotinine antibody fragment and the cotinine-anti-HER2 antibody conjugate prepared in Example 3-1, it was determined whether the chimeric antigen receptor T cells induces cell death of the HER-positive tumor cells by recognizing HER2 on the cell surface.

First, the AU565 cell line, which is an HER2 positive cell, and MDA-MB-231 cell line, which is an HER2 negative cell, were dispensed such that $2\times10^6$ cells were in a 100 mm cell culture container. The dispensed cells were cultured under the same medium and the conditions as in Test Example 2. The cultured cells were counted, and the cells were prepared so that there were $2\times10^7$ cells per 1 mL for the AU565 cell line and $2\times10^7$ cells per 1 mL for the MDA-MB-231 cell line, and carboxyfluorescein succinimidyl ester (CFSE, Invitrogen, US) was added thereto to a concentration of 1 μM and 100 nM, respectively. After reacting at room temperature for 8 minutes so that each cell line was stained to different fluorescence intensities, the results thereof were determined using a flow cytometer (BD Bioscience, US) and shown in FIG. 9A.

As shown in FIG. 9A, the AU565 cell line was stained to a weak fluorescence intensity ($CFSE^{low}$), and the MDA-MB-231 cell line was stained to a strong fluorescence intensity ($CFSE^{high}$).

The stained cells were washed twice with PBS, and the washed cell lines were mixed in 1:1 ratio of $1.5\times10^6$ cells each and dispensed into a 96-well plate. When the dispensed cells were adhered, the cotinine-anti-HER2 antibody conjugate at 1 μg/mL was added thereto and allowed to react at room temperature for 1 hour. After the reaction, the cell lines were washed with a culture medium, counted, and placed in a 5-mL tube so that there were $5\times10^4$ cells. Herein, the chimeric antigen receptor T cells linked with the anti-cotinine antibody fragment were added and cultured for 4 hours or 22 hours under conditions of 5% $CO_2$ and 37° C. Here, the ratio of the chimeric antigen receptor T cells (working cell line, E), and the AU565 and MDA-MB-231 cell lines (target cell line, T) was set to be 0:1, 5:1, or 10:1. After culturing, in order to distinguish dead cells, 0.25 μg of 7-AAD (BD Bioscience, US) was added per $1\times10^6$ cells and reacted at room temperature for 10 minutes, and then was analyzed by a flow cytometer. Here, 7-AAD negative cells and CFSE positive cells were fractionated and analyzed. As a result of the analysis, the rate of cell death of the target cell was calculated according to Equation 1 below, and the result is shown in FIG. 9B.

$$\text{Rate of Apoptosis} = \qquad\qquad [\text{Equation 1}]$$

$$100 - \left[ \frac{\begin{array}{c}\text{Ratio of } AU565 \text{ cells in target cell}\\ \text{line cultured with working } T \text{ cells} \\ \hline \text{Ratio of } MDA\text{-}MB\text{-}231 \text{ cells in target}\\ \text{cell line cultured with working } T \text{ cells}\end{array}}{\begin{array}{c}\text{Ratio of } AU565 \text{ cells}\\ \text{in target cell line cultured}\\ \text{without working } T \text{ cells}\\ \hline \text{Ratio of } MDA\text{-}MB\text{-}231 \text{ cells}\\ \text{in target cell line}\\ \text{cultured without working } T \text{ cells}\end{array}} \times 100 \right]$$

As shown in FIG. 9B, it was confirmed that cell death of AU565, which is an HER2 positive cell line, increased in proportion to the amount of the added chimeric antigen receptor T cells. Thus, it was found that the chimeric antigen receptor T cells linked with the anti-cotinine antibody fragment induces cell death specifically to the binding molecule conjugated with cotinine.

Test Example 8. Confirmation of Cell Death-Inducing Effect of Chimeric Antigen Receptor T Cells by Cotinine-Cytotoxic Agent Conjugate A cotinine-cytotoxic agent conjugate was prepared by Concortis Biotherapeutics, and it was determined whether the conjugate induces cell death of the chimeric antigen receptor T cells prepared in Example 2 by the following method.

Specifically, the chimeric antigen receptor T cells were dispensed in a 96-well plate so that there were $5 \times 10^5$ cells and cultured in a culture medium. A 0, 0.1, 1, 10, 100, or 1000 nM cotinine-cytotoxic agent conjugate was added thereto and cultured for 48 hours under conditions of 5% $CO_2$ and 37° C. For the added cotinine-cytotoxic agent conjugate, a cotinine-duocarmycin single conjugate, a cotinine-DM1 complex conjugate (2×cotinine-4×DM 1), or cotinine-duocarmycin complex conjugate (2×cotinine-4× duocarmycin) was used (FIG. 11). After culturing, living cells were stained with 7-AAD, and cells stained with 7-AAD or with c-myc tag were analyzed by a flow cytometer. As a result of the analysis, the cytotoxicity of the chimeric antigen receptor T cells due to the cotinine-cytotoxic agent conjugate was calculated using Equation 2 below, and the results are shown in FIGS. 10A, 10B and 10C. The T cells prepared in Comparative Example 2 were used as a control group.

$$\text{Relative Viability}(\%) = \qquad\qquad [\text{Equation 2}]$$

$$\frac{\begin{array}{c}\text{Positive rate of } myc \text{ staining in group}\\ \text{with conjugate administration} \times\\ \text{Number of surviving cells in group}\\ \text{with conjugate administration}\end{array}}{\begin{array}{c}\text{Positive rate of } myc \text{ staining in group}\\ \text{without conjugate administration} \times\\ \text{Number of surviving cells in group}\\ \text{without conjugate administration}\end{array}} \times 100$$

As shown in FIGS. 10A, 10B and 10C, it was confirmed that much lower doses of cotinine-cytotoxic agent conjugate can induce cell death of the chimeric antigen receptor T cells linked with the anti-cotinine antibody fragment compared to the T cells of Comparative Example 2.

From the above results, it was found that using the small amount of cotinine-cytotoxic agent conjugate, cell death of the chimeric antigen receptor T cells linked with the anti-cotinine antibody fragment can be induced.

---

The invention claimed is:

1. An isolated chimeric antigen receptor comprising, in the order from the N-terminus to the C-terminus of the chimeric antigen receptor, the following (a)-(d):
   (a) an anti-cotinine single chain Fv (scFv) antibody, wherein the anti-cotinine scFv antibody comprises the amino acid sequence of SEQ ID NO: 1;
   (b) a CD8 (cluster of differentiation 8) hinge domain comprising the sequence of SEQ ID NO: 3;
   (c) a transmembrane domain of CD28 comprising the sequence of SEQ ID NO: 5 or 7; and
   (d) a signal transduction domain selected from the group consisting of the following (i)-(iii):
      (i) a CD28 cytoplasmic region comprising the sequence of SEQ ID NO: 9 or 11,
      (ii) a CD3 zeta cytoplasmic region comprising the sequence of SEQ ID NO: 13, and
      (iii) a CD28 cytoplasmic region comprising the sequence of SEQ ID NO: 9 or 11 and a CD3 zeta cytoplasmic region comprising the sequence of SEQ ID NO: 13.

2. The isolated chimeric antigen receptor of claim 1, wherein the signal transduction domain is the (iii) CD28 cytoplasmic region comprising the sequence of SEQ ID NO: 9 or 11 and CD3 zeta cytoplasmic region comprising the sequence of SEQ ID NO: 13.

3. The isolated chimeric antigen receptor of claim 1, wherein the chimeric antigen receptor comprises the amino acid sequence of SEQ ID NO: 15 or SEQ ID NO: 17.

4. An isolated nucleic acid molecule encoding the chimeric antigen receptor of claim 1.

5. An isolated expression vector comprising the nucleic acid molecule of claim 4.

6. The isolated expression vector of claim 5, wherein the expression vector is a virus vector.

7. The isolated expression vector of claim 6, wherein the virus vector is an adenovirus vector, a retrovirus vector, a lentivirus vector, or an adeno-associated virus vector.

8. An isolated virus comprising the nucleic acid molecule of claim 4.

9. An isolated cell transduced with the virus of claim 8.

10. The isolated cell of claim 9, wherein the cell is a T cell, a natural killer cell, or a macrophage.

* * * * *

SEQUENCE LISTING

```
<160> NUMBER OF SEQ ID NOS: 36

<210> SEQ ID NO 1
<211> LENGTH: 245
<212> TYPE: PRT
<213> ORGANISM: Artificial Sequence
<220> FEATURE:
<223> OTHER INFORMATION: amino acid sequence of Anti-cotinine scFv

<400> SEQUENCE: 1

Glu Leu Asp Leu Thr Gln Thr Pro Ala Ser Val Ser Ala Ala Val Gly
1               5                   10                  15

Gly Thr Val Thr Ile Asn Cys Gln Ser Ser Gln Ser Pro Tyr Ser Asn
            20                  25                  30

Glu Trp Leu Ser Trp Tyr Gln Gln Lys Pro Gly Gln Ala Pro Lys Val
        35                  40                  45

Leu Ile Ser Arg Ile Ser Thr Leu Ala Ser Gly Val Ser Ser Arg Phe
    50                  55                  60

Lys Gly Ser Gly Ser Gly Thr Gln Phe Thr Leu Thr Ile Ser Asp Leu
65                  70                  75                  80

Glu Cys Gly Asp Ala Ala Thr Tyr Phe Cys Ala Gly Gly Tyr Asn Phe
                85                  90                  95
```

Gly Leu Phe Pro Phe Gly Gly Gly Thr Glu Leu Glu Ile Leu Ser Ser
                100                 105                 110

Gly Gly Gly Gly Ser Gly Gly Gly Gly Ser Arg Ser Ser
            115                 120                 125

Gln Ser Val Lys Glu Ser Glu Gly Arg Leu Val Thr Pro Gly Gly Ser
        130                 135                 140

Leu Thr Leu Thr Cys Thr Val Ser Gly Ile Asp Leu Ser Arg Asp Trp
145                 150                 155                 160

Met Asn Trp Val Arg Gln Ala Pro Gly Glu Leu Glu Trp Ile Gly
                165                 170                 175

Ala Ile Gly Arg Ser Gly Asp Thr Tyr Tyr Ala Thr Trp Ala Lys Gly
                180                 185                 190

Arg Phe Thr Ile Ser Lys Thr Ser Arg Thr Val Thr Leu Thr Val
                195                 200                 205

Thr Asp Leu Gln Arg Ser Asp Thr Ala Thr Tyr Phe Cys Ala Arg Ile
        210                 215                 220

Pro Tyr Phe Gly Trp Asn Asn Gly Asp Ile Trp Gly Pro Gly Thr Leu
225                 230                 235                 240

Val Thr Ile Ser Ser
                245

<210> SEQ ID NO 2
<211> LENGTH: 735
<212> TYPE: DNA
<213> ORGANISM: Artificial Sequence
<220> FEATURE:
<223> OTHER INFORMATION: nucleotide sequence of Anti-cotinine scFv

<400> SEQUENCE: 2
gagctcgatc tgacccagac tccagcctcc gtgtctgcag ctgtgggagg cacagtcacc      60
atcaattgcc agtccagtca gagtccttat agtaacgagt ggttatcctg gtatcagcag     120
aaaccagggc aggctcccaa agtcctaatt tctaggatat ccactctggc atctggggtc     180
tcatcgcggt tcaaaggcag tggatctggg acacagttca ctctcaccat aagcgacctg     240
gagtgtggcg acgctgccac ttatttctgt gcaggcggtt ataattttgg tttgtttcct     300
ttcggcggag ggaccgagct ggagatccta tcctctggtg gcggtggctc gggcggtggt     360
gggggtggtt cctctagatc ttcccagtcg gtgaaggagt ccgagggtcg cctggtcacg     420
cctggaggat ccctgacact cacctgcaca gtctctggaa tcgacctcag tagggactgg     480
atgaactggg tccgccaggc tccaggggag gggctggaat ggatcggagc cattggtaga     540
agtggagaca catactacgc gacctgggcg aaaggccgat tcaccatctc caaaacctcg     600
tcgaggacgg tgactctaac agtcaccgat ctgcagcgct cagacacggc cacctatttc     660
tgtgccagaa ttccttattt tggttggaat aatggtgaca tctggggccc aggcaccctg     720
gtcaccatct cttca                                                      735

<210> SEQ ID NO 3
<211> LENGTH: 63
<212> TYPE: PRT
<213> ORGANISM: Artificial Sequence
<220> FEATURE:
<223> OTHER INFORMATION: amino acid sequence of Human CD8 hinge

<400> SEQUENCE: 3

Ser Ala Leu Ser Asn Ser Ile Met Tyr Phe Ser His Phe Val Pro Val
1               5                   10                  15

```
Phe Leu Pro Ala Lys Pro Thr Thr Thr Pro Ala Pro Arg Pro Pro Thr
                 20                  25                  30

Pro Ala Pro Thr Ile Ala Ser Gln Pro Leu Ser Leu Arg Pro Glu Ala
             35                  40                  45

Cys Arg Pro Ala Ala Gly Gly Ala Val His Thr Arg Gly Leu Asp
        50                  55                  60

<210> SEQ ID NO 4
<211> LENGTH: 189
<212> TYPE: DNA
<213> ORGANISM: Artificial Sequence
<220> FEATURE:
<223> OTHER INFORMATION: nucleotide sequence of Human CD8 hinge

<400> SEQUENCE: 4
tcagcgctga gcaactccat catgtacttc agccacttcg tgccggtctt cctgccagcg      60
aagcccacca cgacgccagc gccgcgacca ccaacaccgg cgcccaccat cgcgtcgcag     120 ccctgtccc tgcgcccaga ggcatgccgg ccagcggcgg ggggcgcagt gcacacgagg     180
gggctggat                                                             189

<210> SEQ ID NO 5
<211> LENGTH: 28
<212> TYPE: PRT
<213> ORGANISM: Artificial Sequence
<220> FEATURE:
<223> OTHER INFORMATION: amino acid sequence of Human CD28 Transmembrane
      region

<400> SEQUENCE: 5

Pro Phe Trp Val Leu Val Val Gly Gly Val Leu Ala Cys Tyr Ser
1               5                   10                  15

Leu Leu Val Thr Val Ala Phe Ile Ile Phe Trp Val
                 20                  25

<210> SEQ ID NO 6
<211> LENGTH: 84
<212> TYPE: DNA
<213> ORGANISM: Artificial Sequence
<220> FEATURE:
<223> OTHER INFORMATION: nucleotide sequence of Human CD28 Transmembrane
      region

<400> SEQUENCE: 6
ccctttgggg tgctggtggt ggttggtgga gtcctggctt gctatagctt gctagtaaca      60
gtggccttta ttattttctg ggtg                                             84

<210> SEQ ID NO 7
<211> LENGTH: 30
<212> TYPE: PRT
<213> ORGANISM: Artificial Sequence
<220> FEATURE:
<223> OTHER INFORMATION: amino acid sequence of Mouse CD28 Transmembrane
      region

<400> SEQUENCE: 7

Pro Lys Leu Phe Trp Ala Leu Val Val Val Ala Gly Val Leu Phe Cys
1               5                   10                  15

Tyr Gly Leu Leu Val Thr Val Ala Leu Cys Val Ile Trp Thr
                 20                  25                  30

<210> SEQ ID NO 8
<211> LENGTH: 90
```

```
<212> TYPE: DNA
<213> ORGANISM: Artificial Sequence
<220> FEATURE:
<223> OTHER INFORMATION: nucleotide sequence of Mouse CD28 Transmembrane
      region

<400> SEQUENCE: 8
cctaagctgt tttgggcact ggtcgtggtt gctggagtcc tgttttgtta tggcttgcta      60
gtgacagtgg ctctttgtgt tatctggaca                                      90

<210> SEQ ID NO 9
<211> LENGTH: 41
<212> TYPE: PRT
<213> ORGANISM: Artificial Sequence
<220> FEATURE:
<223> OTHER INFORMATION: amino acid sequence of Human CD28 cytoplasmic
      region

<400> SEQUENCE: 9

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 10
<211> LENGTH: 123
<212> TYPE: DNA
<213> ORGANISM: Artificial Sequence
<220> FEATURE:
<223> OTHER INFORMATION: nucleotide sequence of Human CD28 cytoplasmic
      region

<400> SEQUENCE: 10
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                  123

<210> SEQ ID NO 11
<211> LENGTH: 41
<212> TYPE: PRT
<213> ORGANISM: Artificial Sequence
<220> FEATURE:
<223> OTHER INFORMATION: amino acid sequence of Mouse CD28 cytoplasmic
      region

<400> SEQUENCE: 11

Asn Ser Arg Arg Asn Arg Leu Leu Gln Ser Asp Tyr Met Asn Met Thr
1               5                   10                  15

Pro Arg Arg Pro Gly Leu Thr Arg Lys Pro Tyr Gln Pro Tyr Ala Pro
            20                  25                  30

Ala Arg Asp Phe Ala Ala Tyr Arg Pro
        35                  40

<210> SEQ ID NO 12
<211> LENGTH: 123
<212> TYPE: DNA
<213> ORGANISM: Artificial Sequence
<220> FEATURE:
<223> OTHER INFORMATION: nucleotide sequence of Mouse CD28 cytoplasmic
      region

<400> SEQUENCE: 12
```

```
aatagtagaa ggaacagact ccttcaaagt gactacatga acatgactcc ccggaggcct    60
gggctcactc gaaagcctta ccagccctac gcccctgcca gagactttgc agcgtaccgc   120
ccc                                                                 123
```

<210> SEQ ID NO 13
<211> LENGTH: 112
<212> TYPE: PRT
<213> ORGANISM: Artificial Sequence
<220> FEATURE:
<223> OTHER INFORMATION: amino acid sequence of Human CD3 zeta
      cytoplasmic region

<400> SEQUENCE: 13

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 14
<211> LENGTH: 339
<212> TYPE: DNA
<213> ORGANISM: Artificial Sequence
<220> FEATURE:
<223> OTHER INFORMATION: nucleotide sequence of Human CD3 zeta
      cytoplasmic region

<400> SEQUENCE: 14

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgctaa                          339
```

<210> SEQ ID NO 15
<211> LENGTH: 531
<212> TYPE: PRT
<213> ORGANISM: Artificial Sequence
<220> FEATURE:
<223> OTHER INFORMATION: amino acid sequence of chimeric antigen
      receptor_Human

<400> SEQUENCE: 15

```
Met Asp Phe Gln Val Gln Ile Phe Ser Phe Leu Leu Ile Ser Ala Ser
1               5                   10                  15

Val Ile Met Ser Arg Glu Leu Asp Leu Thr Gln Thr Pro Ala Ser Val
            20                  25                  30
```

-continued

```
Ser Ala Ala Val Gly Gly Thr Val Thr Ile Asn Cys Gln Ser Ser Gln
         35                  40                  45

Ser Pro Tyr Ser Asn Glu Trp Leu Ser Trp Tyr Gln Gln Lys Pro Gly
 50                  55                  60

Gln Ala Pro Lys Val Leu Ile Ser Arg Ile Ser Thr Leu Ala Ser Gly
 65                  70                  75                  80

Val Ser Ser Arg Phe Lys Gly Ser Gly Ser Gly Thr Gln Phe Thr Leu
                 85                  90                  95

Thr Ile Ser Asp Leu Glu Cys Gly Asp Ala Ala Thr Tyr Phe Cys Ala
             100                 105                 110

Gly Gly Tyr Asn Phe Gly Leu Phe Pro Phe Gly Gly Gly Thr Glu Leu
             115                 120                 125

Glu Ile Leu Ser Ser Gly Gly Gly Ser Gly Gly Gly Gly Gly
         130                 135                 140

Ser Ser Arg Ser Ser Gln Ser Val Lys Glu Ser Glu Gly Arg Leu Val
145                 150                 155                 160

Thr Pro Gly Gly Ser Leu Thr Leu Thr Cys Thr Val Ser Gly Ile Asp
                 165                 170                 175

Leu Ser Arg Asp Trp Met Asn Trp Val Arg Gln Ala Pro Gly Glu Gly
             180                 185                 190

Leu Glu Trp Ile Gly Ala Ile Gly Arg Ser Gly Asp Thr Tyr Tyr Ala
         195                 200                 205

Thr Trp Ala Lys Gly Arg Phe Thr Ile Ser Lys Thr Ser Ser Arg Thr
     210                 215                 220

Val Thr Leu Thr Val Thr Asp Leu Gln Arg Ser Asp Thr Ala Thr Tyr
225                 230                 235                 240

Phe Cys Ala Arg Ile Pro Tyr Phe Gly Trp Asn Asn Gly Asp Ile Trp
                 245                 250                 255

Gly Pro Gly Thr Leu Val Thr Ile Ser Ser Ala Ala Ala Glu Gln Lys
             260                 265                 270

Leu Ile Ser Glu Glu Asp Leu Asn Gly Val Thr Val Ser Ser Ala Leu
         275                 280                 285

Ser Asn Ser Ile Met Tyr Phe Ser His Phe Val Pro Val Phe Leu Pro
 290                 295                 300

Ala Lys Pro Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                 325                 330                 335

Ala Ala Gly Gly Ala Val His Thr Arg Gly Leu Asp Pro Phe Trp Val
             340                 345                 350

Leu Val Val Val Gly Gly Val Leu Ala Cys Tyr Ser Leu Leu Val Thr
         355                 360                 365

Val Ala Phe Ile Ile Phe Trp Val Arg Ser Lys Arg Ser Arg Leu Leu
     370                 375                 380

His Ser Asp Tyr Met Asn Met Thr Pro Arg Arg Pro Gly Pro Thr Arg
385                 390                 395                 400

Lys His Tyr Gln Pro Tyr Ala Pro Pro Arg Asp Phe Ala Ala Tyr Arg
                 405                 410                 415

Ser Leu Glu Arg Val Lys Phe Ser Arg Ser Ala Asp Ala Pro Ala Tyr
             420                 425                 430

Gln Gln Gly Gln Asn Gln Leu Tyr Asn Glu Leu Asn Leu Gly Arg Arg
         435                 440                 445

Glu Glu Tyr Asp Val Leu Asp Lys Arg Arg Gly Arg Asp Pro Glu Met
```

|   |   |   |   |   | 450 |   |   |   |   |   | 455 |   |   |   |   |   | 460 |   |   |
|---|---|---|---|---|---|---|---|---|---|---|---|---|---|---|---|---|---|---|---|

Gly Gly Lys Pro Arg Arg Lys Asn Pro Gln Glu Gly Leu Tyr Asn Glu
465                      470                  475                  480

Leu Gln Lys Asp Lys Met Ala Glu Ala Tyr Ser Glu Ile Gly Met Lys
                  485                  490                  495

Gly Glu Arg Arg Arg Gly Lys Gly His Asp Gly Leu Tyr Gln Gly Leu
            500                  505                  510

Ser Thr Ala Thr Lys Asp Thr Tyr Asp Ala Leu His Met Gln Ala Leu
        515                  520                  525

Pro Pro Arg
    530

<210> SEQ ID NO 16
<211> LENGTH: 1596
<212> TYPE: DNA
<213> ORGANISM: Artificial Sequence
<220> FEATURE:
<223> OTHER INFORMATION: nucleotide sequence of chimeric antigen
     receptor_Human

<400> SEQUENCE: 16

| | | | | | |
|---|---|---|---|---|---|
| atggattttc | aggtgcagat | tttcagcttc | ctgctaatca | gtgcctcagt | cataatgtct | 60 |
| agagagctcg | atctgaccca | gactccagcc | tccgtgtctg | cagctgtggg | aggcacagtc | 120 |
| accatcaatt | gccagtccag | tcagagtcct | tatagtaacg | agtggttatc | ctggtatcag | 180 |
| cagaaaccag | gcaggctcc | caaagtccta | atttctagga | tatccactct | ggcatctggg | 240 |
| gtctcatcgc | ggttcaaagg | cagtggatct | gggacacagt | tcactctcac | cataagcgac | 300 |
| ctggagtgtg | gcgacgctgc | cacttatttc | tgtgcaggcg | ttataattt | ggtttgttt | 360 |
| cctttcggcg | gagggaccga | gctggagatc | ctatcctctg | gtggcggtgg | ctcgggcggt | 420 |
| ggtggggtg | gttcctctag | atcttcccag | tcggtgaagg | agtccgaggg | tcgcctggtc | 480 |
| acgcctggag | gatccctgac | actcacctgc | acagtctctg | gaatcgacct | cagtagggac | 540 |
| tggatgaact | gggtccgcca | ggctccaggg | gaggggctgg | aatggatcgg | agccattggt | 600 |
| agaagtggag | acacatacta | cgcgacctgg | gcgaaaggcc | gattaccat | ctccaaaacc | 660 |
| tcgtcgagga | cggtgactct | aacagtcacc | gatctgcagc | gctcagacac | ggccacctat | 720 |
| ttctgtgcca | gaattcctta | ttttggttgg | ataatggtg | acatctgggg | cccaggcacc | 780 |
| ctggtcacca | tctcttcagc | ggccgcagaa | caaaaactca | tctcagaaga | ggatctgaat | 840 |
| ggggtcaccg | tctcttcagc | gctgagcaac | tccatcatgt | acttcagcca | cttcgtgccg | 900 |
| gtcttcctgc | cagcgaagcc | caccacgacg | ccagcgccgc | gaccaccaac | accggcgccc | 960 |
| accatcgcgt | cgcagcccct | gtccctgcgc | ccagaggcat | gccggccagc | ggcgggggc | 1020 |
| gcagtgcaca | cgagggggct | ggatcccttt | tgggtgctgg | tggtggttgg | tggagtcctg | 1080 |
| gcttgctata | gcttgctagt | aacagtggcc | tttattattt | tctgggtgag | gagtaagagg | 1140 |
| agcaggctcc | tgcacagtga | ctacatgaac | atgactcccc | gccgcccgg | gcccaccgc | 1200 |
| aagcattacc | agccctatgc | cccaccacgc | gacttcgcag | cctatcgctc | cctcgagaga | 1260 |
| gtgaagttca | gcaggagcgc | agacgccccc | gcgtaccagc | agggccagaa | ccagctctat | 1320 |
| aacgagctca | atctaggacg | aagagaggag | tacgatgttt | tggacaagag | acgtggccgg | 1380 |
| gaccctgaga | tggggggaaa | gccgagaagg | aagaaccctc | aggaaggcct | gtacaatgaa | 1440 |
| ctgcagaaaa | ataagatggc | ggaggcctac | agtgagattg | gatgaaagg | cgagcgccgg | 1500 |
| aggggcaagg | ggcacgatgg | cctttaccag | ggtctcagta | cagccaccaa | ggacacctac | 1560 | gacgcccttc acatgcaggc cctgccccct cgctaa        1596

<210> SEQ ID NO 17
<211> LENGTH: 533
<212> TYPE: PRT
<213> ORGANISM: Artificial Sequence
<220> FEATURE:
<223> OTHER INFORMATION: amino acid sequence of chimeric antigen receptor_Mouse

<400> SEQUENCE: 17

```
Met Asp Phe Gln Val Gln Ile Phe Ser Phe Leu Leu Ile Ser Ala Ser
1               5                   10                  15

Val Ile Met Ser Arg Glu Leu Asp Leu Thr Gln Thr Pro Ala Ser Val
            20                  25                  30

Ser Ala Ala Val Gly Gly Thr Val Thr Ile Asn Cys Gln Ser Ser Gln
        35                  40                  45

Ser Pro Tyr Ser Asn Glu Trp Leu Ser Trp Tyr Gln Gln Lys Pro Gly
    50                  55                  60

Gln Ala Pro Lys Val Leu Ile Ser Arg Ile Ser Thr Leu Ala Ser Gly
65                  70                  75                  80

Val Ser Ser Arg Phe Lys Gly Ser Gly Ser Gly Thr Gln Phe Thr Leu
                85                  90                  95

Thr Ile Ser Asp Leu Glu Cys Gly Asp Ala Ala Thr Tyr Phe Cys Ala
            100                 105                 110

Gly Gly Tyr Asn Phe Gly Leu Phe Pro Phe Gly Gly Gly Thr Glu Leu
        115                 120                 125

Glu Ile Leu Ser Ser Gly Gly Gly Ser Gly Gly Gly Gly Gly
    130                 135                 140

Ser Ser Arg Ser Ser Gln Ser Val Lys Glu Ser Glu Gly Arg Leu Val
145                 150                 155                 160

Thr Pro Gly Gly Ser Leu Thr Leu Thr Cys Thr Val Ser Gly Ile Asp
                165                 170                 175

Leu Ser Arg Asp Trp Met Asn Trp Val Arg Gln Ala Pro Gly Glu Gly
            180                 185                 190

Leu Glu Trp Ile Gly Ala Ile Gly Arg Ser Gly Asp Thr Tyr Tyr Ala
        195                 200                 205

Thr Trp Ala Lys Gly Arg Phe Thr Ile Ser Lys Thr Ser Ser Arg Thr
    210                 215                 220

Val Thr Leu Thr Val Thr Asp Leu Gln Arg Ser Asp Thr Ala Thr Tyr
225                 230                 235                 240

Phe Cys Ala Arg Ile Pro Tyr Phe Gly Trp Asn Asn Gly Asp Ile Trp
                245                 250                 255

Gly Pro Gly Thr Leu Val Thr Ile Ser Ser Ala Ala Ala Glu Gln Lys
            260                 265                 270

Leu Ile Ser Glu Glu Asp Leu Asn Gly Val Thr Val Ser Ser Ala Leu
        275                 280                 285

Ser Asn Ser Ile Met Tyr Phe Ser His Phe Val Pro Val Phe Leu Pro
    290                 295                 300

Ala Lys Pro Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Pro Lys Leu Phe
            340                 345                 350
```

```
Trp Ala Leu Val Val Ala Gly Val Leu Phe Cys Tyr Gly Leu Leu
        355                 360                 365

Val Thr Val Ala Leu Cys Val Ile Trp Thr Asn Ser Arg Arg Asn Arg
    370                 375                 380

Leu Leu Gln Ser Asp Tyr Met Asn Met Thr Pro Arg Arg Pro Gly Leu
385                 390                 395                 400

Thr Arg Lys Pro Tyr Gln Pro Tyr Ala Pro Ala Arg Asp Phe Ala Ala
                405                 410                 415

Tyr Arg Pro Leu Glu Arg Val Lys Phe Ser Arg Ser Ala Asp Ala Pro
                420                 425                 430

Ala Tyr Gln Gln Gly Gln Asn Gln Leu Tyr Asn Glu Leu Asn Leu Gly
            435                 440                 445

Arg Arg Glu Glu Tyr Asp Val Leu Asp Lys Arg Arg Gly Arg Asp Pro
        450                 455                 460

Glu Met Gly Gly Lys Pro Arg Arg Lys Asn Pro Gln Glu Gly Leu Tyr
465                 470                 475                 480

Asn Glu Leu Gln Lys Asp Lys Met Ala Glu Ala Tyr Ser Glu Ile Gly
                485                 490                 495

Met Lys Gly Glu Arg Arg Arg Gly Lys Gly His Asp Gly Leu Tyr Gln
            500                 505                 510

Gly Leu Ser Thr Ala Thr Lys Asp Thr Tyr Asp Ala Leu His Met Gln
        515                 520                 525

Ala Leu Pro Pro Arg
    530

<210> SEQ ID NO 18
<211> LENGTH: 1602
<212> TYPE: DNA
<213> ORGANISM: Artificial Sequence
<220> FEATURE:
<223> OTHER INFORMATION: nucleotide sequence of chimeric antigen
      receptor_Mouse

<400> SEQUENCE: 18
atggattttc aggtgcagat tttcagcttc ctgctaatca gtgcctcagt cataatgtct      60
agagagctcg atctgaccca gactccagcc tccgtgtctg cagctgtggg aggcacagtc     120
accatcaatt gccagtccag tcagagtcct tatagtaacg agtggttatc ctggtatcag     180
cagaaaccag gcaggctccc aaagtcctaa atttctagga tatccactct ggcatctggg     240
gtctcatcgc ggttcaaagg cagtggatct gggacacagt tcactctcac cataagcgac     300
ctggagtgtg cgacgctgc cacttatttc tgtgcaggcg gttataattt tggtttgttt     360
cctttcggcg gagggaccga gctggagatc ctatcctctg gtggcggtgg ctcgggcggt     420
ggtgggggtg gttcctctag atcttcccag tcggtgaagg agtccgaggg tcgcctggtc     480
acgcctggag atccctgac actcacctgc acagtctctg gaatcgacct cagtagggac     540
tggatgaact gggtccgcca ggctccaggg aggggctgg aatggatcgg agccattggt     600
agaagtggag acacatacta cgcgacctgg gcgaaaggcc gattcaccat ctccaaaacc     660
tcgtcgagga cggtgactct aacagtcacc gatctgcagc gctcagacac ggccacctat     720
ttctgtgcca gaattcctta ttttggttgg aataatggtg acatctgggg cccaggcacc     780
ctggtcacca tctcttcagc ggccgcagaa caaaaactca tctcagaaga ggatctgaat     840
gggggtcacc tctcttcagc gctgagcaac tccatcatgt acttcagcca cttcgtgccg     900
gtcttcctgc agcgaagcc accacgacg ccagcgccgc gaccaccaac accggcgccc     960
```

-continued

```
accatcgcgt cgcagcccct gtccctgcgc ccagaggcat gccggccagc ggcgggggc      1020 gcagtgcaca cgagggggct ggatcctaag ctgttttggg cactggtcgt ggttgctgga      1080
gtcctgtttt gttatggctt gctagtgaca gtggctcttt gtgttatctg acaaatagt      1140 agaaggaaca gactccttca aagtgactac atgaacatga ctccccggag cctgggctc      1200 actcgaaagc cttaccagcc ctacgcccct gccagagact ttgcagcgta ccgccccctc      1260
gagagagtga agttcagcag gagcgcagac gccccgcgt accagcaggg ccagaaccag      1320
ctctataacg agctcaatct aggacgaaga gaggagtacg atgttttgga caagagacgt      1380
ggccgggacc ctgagatggg gggaaagccg agaaggaaga accctcagga aggcctgtac      1440
aatgaactgc agaaagataa gatggcggag gcctacagtg agattgggat gaaaggcgag      1500
cgccggaggg gcaaggggca cgatggcctt taccagggtc tcagtacagc caccaaggac      1560
acctacgacg cccttcacat gcaggccctg ccccctcgct aa                        1602
```

<210> SEQ ID NO 19
<211> LENGTH: 21
<212> TYPE: PRT
<213> ORGANISM: Artificial Sequence
<220> FEATURE:
<223> OTHER INFORMATION: amino acid sequence of Mouse Ig kappa leader

<400> SEQUENCE: 19

```
Met Asp Phe Gln Val Gln Ile Phe Ser Phe Leu Leu Ile Ser Ala Ser
1               5                   10                  15

Val Ile Met Ser Arg
            20
```

<210> SEQ ID NO 20
<211> LENGTH: 63
<212> TYPE: DNA
<213> ORGANISM: Artificial Sequence
<220> FEATURE:
<223> OTHER INFORMATION: nucleotide sequence of Mouse Ig kappa leader

<400> SEQUENCE: 20

```
atggattttc aggtgcagat tttcagcttc ctgctaatca gtgcctcagt cataatgtct      60
aga                                                                    63
```

<210> SEQ ID NO 21
<211> LENGTH: 10
<212> TYPE: PRT
<213> ORGANISM: Artificial Sequence
<220> FEATURE:
<223> OTHER INFORMATION: amino acid sequence of C-myc tag epitope

<400> SEQUENCE: 21

```
Glu Gln Lys Leu Ile Ser Glu Glu Asp Leu
1               5                   10
```

<210> SEQ ID NO 22
<211> LENGTH: 30
<212> TYPE: DNA
<213> ORGANISM: Artificial Sequence
<220> FEATURE:
<223> OTHER INFORMATION: nucleotide sequence of C-myc tag epitope

<400> SEQUENCE: 22

```
gaacaaaaac tcatctcaga agaggatctg                                       30
```

```
<210> SEQ ID NO 23
<211> LENGTH: 5
<212> TYPE: PRT
<213> ORGANISM: Artificial Sequence
<220> FEATURE:
<223> OTHER INFORMATION: amino acid sequence of CDR1 at heavy chain
      variable region of Anti-cotinine scFv

<400> SEQUENCE: 23

Arg Asp Trp Met Asn
1               5

<210> SEQ ID NO 24
<211> LENGTH: 15
<212> TYPE: PRT
<213> ORGANISM: Artificial Sequence
<220> FEATURE:
<223> OTHER INFORMATION: amino acid sequence of CDR2 at heavy chain
      variable region of Anti-cotinine scFv

<400> SEQUENCE: 24

Ala Ile Gly Arg Ser Gly Asp Thr Tyr Tyr Ala Thr Trp Ala Lys
1               5                   10                  15

<210> SEQ ID NO 25
<211> LENGTH: 11
<212> TYPE: PRT
<213> ORGANISM: Artificial Sequence
<220> FEATURE:
<223> OTHER INFORMATION: amino acid sequence of CDR3 at heavy chain
      variable region of Anti-cotinine scFv

<400> SEQUENCE: 25

Ile Pro Tyr Phe Gly Trp Asn Asn Gly Asp Ile
1               5                   10

<210> SEQ ID NO 26
<211> LENGTH: 13
<212> TYPE: PRT
<213> ORGANISM: Artificial Sequence
<220> FEATURE:
<223> OTHER INFORMATION: amino acid sequence of CDR1 at light chain
      variable region of Anti-cotinine scFv

<400> SEQUENCE: 26

Gln Ser Ser Gln Ser Pro Tyr Ser Asn Glu Trp Leu Ser
1               5                   10

<210> SEQ ID NO 27
<211> LENGTH: 7
<212> TYPE: PRT
<213> ORGANISM: Artificial Sequence
<220> FEATURE:
<223> OTHER INFORMATION: amino acid sequence of CDR2 at light chain
      variable region of Anti-cotinine scFv

<400> SEQUENCE: 27

Arg Ile Ser Thr Leu Ala Ser
1               5

<210> SEQ ID NO 28
<211> LENGTH: 12
<212> TYPE: PRT
<213> ORGANISM: Artificial Sequence
<220> FEATURE:
<223> OTHER INFORMATION: amino acid sequence of CDR3 at light chain
      variable region of Anti-cotinine scFv

<400> SEQUENCE: 28
```

Ala Gly Gly Tyr Asn Phe Gly Leu Phe Pro Phe Gly
 1               5                  10

<210> SEQ ID NO 29
<211> LENGTH: 99
<212> TYPE: DNA
<213> ORGANISM: Artificial Sequence
<220> FEATURE:
<223> OTHER INFORMATION: anti-cotinine scFv forward primer

<400> SEQUENCE: 29
gatatcaagc ttgccaccat ggattttcag gtgcagattt tcagcttcct gctaatcagt    60
gcctcagtca taatgtctag agagctcgat ctgacccag                            99

<210> SEQ ID NO 30
<211> LENGTH: 18
<212> TYPE: DNA
<213> ORGANISM: Artificial Sequence
<220> FEATURE:
<223> OTHER INFORMATION: anti-cotinine scFv reverse primer

<400> SEQUENCE: 30
tgaagagatg gtgaccag                                                   18

<210> SEQ ID NO 31
<211> LENGTH: 18
<212> TYPE: DNA
<213> ORGANISM: Artificial Sequence
<220> FEATURE:
<223> OTHER INFORMATION: CAR skeleton forward primer

<400> SEQUENCE: 31
gcggccgcag aacaaaaa                                                   18

<210> SEQ ID NO 32
<211> LENGTH: 30
<212> TYPE: DNA
<213> ORGANISM: Artificial Sequence
<220> FEATURE:
<223> OTHER INFORMATION: CAR skeleton reverse primer

<400> SEQUENCE: 32
actagtgtcg acttagcgag ggggcagggc                                      30

<210> SEQ ID NO 33
<211> LENGTH: 42
<212> TYPE: DNA
<213> ORGANISM: Artificial Sequence
<220> FEATURE:
<223> OTHER INFORMATION: CEA CAR forward primer

<400> SEQUENCE: 33
gatatcaagc ttccatgggc caccatggat tttcaggtgc ag                        42

<210> SEQ ID NO 34
<211> LENGTH: 44
<212> TYPE: DNA
<213> ORGANISM: Artificial Sequence
<220> FEATURE:
<223> OTHER INFORMATION: CEA CAR reverse primer

<400> SEQUENCE: 34
gaattcatcg atgtcgacgc ggccgcttag cgagggggca gggc                      44

```
<210> SEQ ID NO 35
<211> LENGTH: 27
<212> TYPE: RNA
<213> ORGANISM: Artificial Sequence
<220> FEATURE:
<223> OTHER INFORMATION: pegaptanib RNA aptamer

<400> SEQUENCE: 35
cggaaucagu gaaugcuuau acauccg                                         27

<210> SEQ ID NO 36
<211> LENGTH: 28
<212> TYPE: DNA
<213> ORGANISM: Artificial Sequence
<220> FEATURE:
<223> OTHER INFORMATION: control aptamer

<400> SEQUENCE: 36
ttggtggtgg tggttgtggt ggtggtgg                                        28
```